United States Patent [19]
Embleton et al.

[11] Patent Number: 5,830,663
[45] Date of Patent: Nov. 3, 1998

[54] IN SITU RECOMBINANT PCR WITHIN SINGLE CELLS

[75] Inventors: Michael J. Embleton, Nottingham; Guy Gorochov, Cambridge; Peter T. Jones, Cambridge; Gregory P. Winter, Cambridge, all of United Kingdom

[73] Assignee: Medical Research Council, England

[21] Appl. No.: 190,199

[22] PCT Filed: Aug. 10, 1992

[86] PCT No.: PCT/GB92/01483

§ 371 Date: Jul. 13, 1994

§ 102(e) Date: Jul. 13, 1994

[87] PCT Pub. No.: WO93/03151

PCT Pub. Date: Feb. 18, 1993

[30] Foreign Application Priority Data

Aug. 10, 1991 [GB] United Kingdom .................. 9117352
Jun. 11, 1992 [GB] United Kingdom .................. 9212419

[51] Int. Cl.$^6$ .............................. C12Q 1/68; C12P 19/34; C07H 21/02
[52] U.S. Cl. .............................. 435/6; 435/911; 435/912; 435/914; 435/172.3; 536/243; 536/24.31; 536/24.32; 536/24.33
[58] Field of Search .............................. 435/6, 91.1, 91.2, 435/172.3, 91.4, 820.1; 536/24.3, 24.31, 24.32, 24.33; 935/22, 23, 77, 78, 79; 530/387.1

[56] References Cited

PUBLICATIONS

Dialog Information Services, file 154, Medline 66–91/May, accession No. 07690409, Medline acession No. 91209490, Marks J.D. et al: "Oligonucleotide primers for polymerase chain reaction amplification of human immunoglobulin variable genes and design of family–specific oligonucleotide probes", Eur J Immunol Apr. 1991, 21 (4) pp. 985–991.

Haase et al: "Amplification and detection of lentiviral DNA inside cells", Proc.Natl. Acad. Sci.USA, vol. 87, Jul. 1990, see pp. 4971–4975.

Orlandi et al: "Cloning immunoglobulin variable domains for expression by the polymerase chain reaction", Proc.Natl.Acad.Sci. USA, vol. 86, May 1989, see pp. 3833–3837.

Clackson et al: "Sticky feet–directed mutagenesis and its application to swapping antibody domainssss", Nucleic Acids Research, vol. 17, No. 24, 1989, see pp. 10163–10170.

Ward et al: "Binding activities of a repertorire of single immunoglobulin variable domains secreted from *Escherichia coli*", Nature, vol. 341, Oct. 1989, see pp. 544–546.

Haase et al, "Amplification and detection of lentiviral DNA inside cells", Proc. Natl. Acad. Sci. 87:4971–4975, Jul. 1990.

Kawasaki, E., "Amplification of RNA" in PCR Protocols: A Guide to Methods and Applications, (Ed. Innis) Academic Press, pp. 21–27, 1990.

Higuchi, R., "Recombinant PCR" in PCR Protocols: A Guide to Methods and Applications, (Ed. Innis) Academic Press, pp. 177–183, 1990.

Chehab et al, "Detection of specific DNA sequences by fluorescence amplification: A color complementation assay", Proc. Natl. Acad. Sci. 86:9178–9182, Dec. 1989.

Tecott et al, "In situ transcription: Specific synthesis of complementary DNA in fixed tissue sections", Science 240:1661–1664, Jun. 1988.

Mogensen et al, "Nonradioactive, sequence detection of RNA in situ by primed in situ labeling", Exp. Cell Res. 196:92–98, 1991.

Spann et al, "In situ amplification of single copy gene segments in individual cells by the polymerase chain reaction", Infection 19(4):242–244, Jul. 1991.

*Primary Examiner*—W. Gary Jones
*Assistant Examiner*—Jeffrey Fredman
*Attorney, Agent, or Firm*—Cushman Darby & Cushman IP Group of Pillsbury Madison & Sutro

[57] ABSTRACT

Disclosed is a method of treating a heterogeneous population of cells to link together copies of two or more nucleic acid sequences from at least some of the cells, the arrangement being such that copies of the DNA sequences from an individual cell are preferentially linked in the vicinity of the nucleic acid from which the copies are derived. Also disclosed are recombinant proteins expressed by the method of the invention and kits for performing said method.

10 Claims, 13 Drawing Sheets scFV(INK3) NQ2/12.4 WITH OLIGOS

```
              Q  V  Q  L  K  E  S  G  P  G  L  V  A  P  S  Q  S  L  S  I
              CAGGTGCAGCTGAAGGAGTCAGGACCTGGCCTGGTGGCCCCTCACAGAGCCTGTCCATC
                                         [NQ2/12.4BKNES] 5'-cgccctcacagagcctgtcca-3'
                 [NQ2/12.4 back] 5'-caggtgcagctgaaggagtcagg-3'
                                                            3'-GGAGTGTCTCGGACAGGTAG-5' [NQ2HPRB]
                                            VH NQ2/12.4
  T  C  T  V  S  G  F  S  L  T  S  Y  G  V  H  W  M  V  R  Q  P  P  G  K  G  L  E  W  L  G  V  I  W  A  G  G  S  T  N  Y  N
  ACTTGCACTGTCTCTGGGTTTTCATTAACCAGCTATGGTGTGCACTGGGTCTGGAGTGGCTGGGAGTAATATGGGCTGGTGGAAGCACAAATTATAAT S  A  L  M  S  R  L  S  I  S  K  D  N  S  K  S  Q  V  F  L  K  M  N  S  L  Q  T  D  D  T  A  M  Y  Y  C  A  R  D  R  G
  TCGGCTCTCATGTCCAGACTGAGCATCAGCAAGACAACTCCAAGAGCCAAGTTTTCTTAAAAATGAACAGTCTGCAAACTGATGACACAGCCATGTACTACTGTGCCAGAGATCGGGGG
```

FIG. 2A

```
A  Y  W  G  Q  G  T  L  V  T  V  S  A G G G G S G G G G S G G G G S  Q  I  V  L  T  Q  S  P  A  I  M  S
GCTTACTGGGGCCAAGGGACTCTGGTCACTGTCTCTGCAGGTGGTGGTGGTTCTGGCGGCGGCGGCTCTGGTGGTGGTGGATCTCAAATTGTTCTCACCCAGTCTCCAGCAATCATGTCT
              3'-GACCAGTGACAGAGACGTCCACTGCCACCACCAAGACCGCCGCCGCCGAGACCACCACCACCTAGAGTTTAACAAGAGTGGTCAGAGGTCGTTAGTACAG-5' [MoVh1nk3]
                                                                                           |||||||||||||||||||||||
                                                             [MoVk1nk3] 5'-gcggtggtggcggcagtggcggcggctctcaaattgttctcaccagtctccagc-3'

A  S  P  G  Q  K  V  T  M  T  C  S  A  S  S  S  V  S  Y  M  H  W  Y  Q  Q  K  S  G  T  S  P  K  R  W  I  Y  D  T  S  K
GCATCTCCAGGCCAGAAGGTCACCATGACCTGCAGCGCCAGCTCAAGTGTAAGTTACATGCACTGGTACCAGCAGAAGTCAGGCACCTCCCCCAAAAGATGGATTTATGACACATCCAAA
                                                                       3'-AATGTACGTGACCATGGTC-5' [NQ2kPRB]

VkNQ2/12.4

A  S  G  V  P  A  R  F  S  G  S  G  S  A  T  S  Y  S  L  T  I  S  S  M  E  A  E  D  A  A  T  Y  Y  C  Q  Q  W  S  S
CTGGCTTCTGGAGTCCCTGCTCGCTTCAGTGGCAGTGGGTCTGCGACCTCTTACTCTCTCACAATCAGCAGCATGGAGGCTGAAGATGCTGCCACTTATTACTGCCAGCAGTGGAGTAGT

N  P  L  T  F  G  A  G  T  K  L  E  L  K  P
AACCCACTCACGTTCGGTGCTGGGACCAAGCTGGAGCTGAAACGTAAG........
                3'-GGTGAGTGCAAGCCACGACCC-5' [MoJk5FOR2]
```

FIG. 2B sc(INK4)Fv NQ10/12.5 WITH OLIGOS

```
        D  V  Q  L  V  E  S  G  G  G  L  V  Q  P  G  G  S  R  K  L  S  C  A  A  S  G
     GATGTGCAGCTGGTGGAGTCTGGGGGAGGCTTAGTGCAGCCTGGAGGGTCCCGGAAACTCTCCTGTGCAGCCTCTGGA
                                        [NQ10/12.5BKNES] 5'-agcctggagggtccccggaaac
[NQ10/12.5 back]  5'- tgcagctggtgtggagtctgggggg-3'

3'-GACCTCCCAGGGCCTTTGAG-5' [NQHPRB]

F  T  F  S  S  F  G  M  H  W  V  R  Q  A  P  E  K  G  L  E  W  V  A  Y  I  S  S  G  G  S  T  I  Y  Y
     TTCACTTTCAGTAGCTTTGGAATGCCACTGGGTCGTCAGGCTCCAGAGAAGGGGCTGGAGTGGGTCGCATATATTAGTAGTGGCAGTAGTACCATCTACTAT
```

```
A  D  T  V  K  G  R  F  T  I  S  R  D  N  P  K  N  T  L  F  L  Q  M  T  S  L  R  S  E  D  T  A  M  Y  Y  C  A  R  D  Y
GCAGACACAGTGAAGGGCCGATTCACCATCTCCAGAGACAATCCCAAGAACACCCTGTTCCTGCAAATGACCAGTCTAAGGTCTGAGGACACGGCCATGTATTACTGTGCAAGAGATTAC
```

LINKER (CONTAINING NheI SITE TO FACILITATE FURTHER CLONING OF PEPTIDE LINKER).

```
G  A  Y  W  G  Q  G  T  L  V  T  V  S  A  A  S  Q  I  V  L  T  Q  S  P  A  I  M  S  A  S  P  G  E  K  V  T  M  T  C
GGGGCTTATTGGGGCCAAGGGACTCTGGTCACTGTCTCTGCAGCTAGCCAAATTGTTCTCACCCAGTCTCCAGCAATCATGTCTGCATCTCCAGGGGAGAAGTCACCATGACCTGC
                                           3'-ACCCCGGTTCCCTGAGACCAGTGACAGAGACGTCGATCGGTTTAAC-5'   [MoVHlnk4]
                                              ||||||||||||||||||||||||||||||||||||||||||||||
                           [MoVklnk4]  5'-cactgtctctgcagctagcaaattgttctcaccagtctccag-3'
```

```
S  A  S  S  S  V  R  Y  M  N  W  F  Q  Q  K  S  G  T  S  P  K  R  W  I  Y  D  T  S  K  L  S  S  G  V  P  A  R  F  S  G
AGTGCCAGTTCAAGTGTAAGGTACATGAACTGGTTCCAACAGAAGTCAGGCACCTCCCCCAAAAGATGGATTTATGACACATCCAAACTGTCTTCTGGAGTCCCTGCTCGCTTCAGTGGC
                      3'-CATGTACTTGACCAAGGTT-5'   [NQ10KPRB]
```

VκNQ10/12.5

```
S  G  S  G  T  S  Y  S  L  T  I  S  S  M  E  A  E  D  A  A  T  Y  Y  C  Q  Q  W  S
AGTGGGTCTGGGACCTCTTACTCTCTCACAATCAGCAGCATGGAGGCTGAAGATGCTGCCACTTATTACTGCCAGCAGTGGAGT
```

```
S  N  P  L  T  F  G  A  G  T  K  L  E  L  K  P
AGTAATCCACTCACGTTCGGTGCTGGGACCAAGCTGGAGCTGAAACGTAAG........
                        3'-GGTGAGTGCAAGCCACGACCC-5'  [MoK5FORNES]
                                   3'-GGTTCGACCTCGACTTTGCATTC-5'  [MoJk5FOR2]
```

FIG. 3B sc(INK3)FvNQ10/12.5 WITH OLIGOS

```
                            D  V  Q  L  V  E  S  G  G  G  L  V  Q  P  G  G  S  R  K  L
                        5'-GATGTGCAGCTGGTGGAGTCTGGGGGAGGCTTAGTGCAGCCTGGAGGTCCCGGAAACTC
                                          [NQ10/12.5BKNES]  5'-agcctggagggtcccggaaac
             [NQ10/12.5 back] 5'-tgcagctggtggagtctgggggg-3'

3'-GACCTCCCAGGGCCTTTGAG-5' [NQ10HPRB]

S  C  A  A  S  G  F  T  F  S  S  F  G  M  H  W  V  R  Q  A  P  E  K  G  L  E  W  V  A  Y  I  S  S  G  S  S  T  I  Y  Y
TCCTGTGCAGCCTCTGGATTCACTTTCAGTAGCTTTGGAATGCACTGGGTTCGTCAGGCTCCAGAGAAGGGGCTGGAGTGGGTCGCATATATTAGTAGTGGCAGTAGTACCATCTACTAT

VhNQ10/12.5

A  D  T  V  K  G  R  F  T  I  S  R  D  N  P  K  N  T  L  F  L  Q  M  T  S  L  R  S  E  D  T  A  M  Y  Y  C  A  R  D  Y
GCAGACACAGTGAAGGGCCGATTCACCATCTCCAGAGACAATCCCAAGAACACCCTGTTCCTGCAAATGACCAGTCTAAGGTCTGAGGACACGGCCATGTATTACTGTGCAAGAGATTAC
```

FIG. 4A sc(INK4)Fv NQ2/12.4 WITH OLIGOS

```
             Q  V  Q  L  K  E  S  G  P  G  L  V  A  P  S  Q  S  L  S  I
            CAGGTGCAGCTGAAGGAGTCAGGACCTGGCCTGGTGGCGCCCCTCACAGAGCCTGTCCATC
[NQ2/12.4BKNES] 5'-cgccctcacagagcctgtcca-3'
[NQ2/12.4back] 5'-caggtgcagctgaaggagtcagg-3'
                                                          3'-GGAGTGTCTCGGACAGGTAG-5' [NQ2HPRB]
             T  C  T  V  S  G  F  S  L  T  S  Y  G  V  H  W  V  R  Q  P  P  G  K  G  L  E  W  L  G  V  I  W  A  G  G  S  T  N  Y  N
            ACTTGCACTGTCTCTGGGTTTTCATTAACCAGCTATGGTGTACACTGGGTTCGCCAGCCTCCAGGAAAGGGTCTGGAGTGGCTGGGAGTAATATGGCTGGTGGAAGCACAAATTATAAT
             S  A  L  M  S  R  L  S  I  S  K  D  N  S  K  S  Q  V  F  L  K  M  N  S  L  Q  T  D  D  T  A  M  Y  Y  C  A  R  D  R  G
            TCGGCTCTCATGTCCAGACTGAGCATCAGCAAAGACAACTCCAAGAGCCAAGTTTTCTTAAAAATGAACAGTCTGCAAACTGATGACACAGTCACTGTACTACTGTGCCAGAGATCGGGGG
                                      VHNQ2/12.4
```

FIG. 5A

LINKER (CONTAINING NheI SITE TO FACILITATE FURTHER CLONING OF PEPTIDE LINKER).

A Y W G Q G T L V T V S A A S Q I V L T Q S P A I M S A S P G Q K V T M T C S
GCTTACTGGGCCAAGGACTCTGGTCACTGTCTGCACTGTCTGCAGTAGCCAAATTGTTCTCACCCAGTCTCCAGCAATCATGTCTGCATCTCCAGGCCAGAAGGTCACCATGACCTGCAGT
3'-ACCCCGGTTCCCTGAGACCAGTGACAGAGACGTCGATCGGTTTAAC-5' [MoVH1nk4]
                                              ||||||||||||||||
                [MoVk1nk4] 5'-cactgtctctgcagctagccaaattgttctcacccagtctccag-3'

VkNQ2/12.4

A S S S V S Y M H W Y Q Q K S G T S P K R W I Y D T S K L A S G V P A R F S G S
GCCAGCTCAAGTGTAAGTTACATGCACTGGTACCAGCAGAAGTCAGGCACCTCCCCCAAAGATGATTTATGACACATCCAAACTGGCTTCTGAGTCCCTGCTCGCTTCAGTGGCAGT
                                       3'-AATGTACGTGACCATGGTC-5' [NQ2kPRB]

G S A T S Y S L T I S S M E A E D A A T Y Y C Q Q W
GGGTCTCTGCCACCTCTTACTCCTCACAATCAGCAGCATGGAGGCTGAAGATGCTGCCACTTATTACTGCCAGCAGTGG

S S N P L T F G A G T K L E L K P
AGTAGTAACCCACTCACGTTCGGTGCTGGGACCAAGCTGGAGCTGAAACGTAAG........
                              3'-GGTGAGTGCAAGCCACGACCC-5' [MoJk5FOR2]
      3'-GGTTCGACCTGACTTTGCATTC-5'- [MoK5FORNES]

FIG. 5B

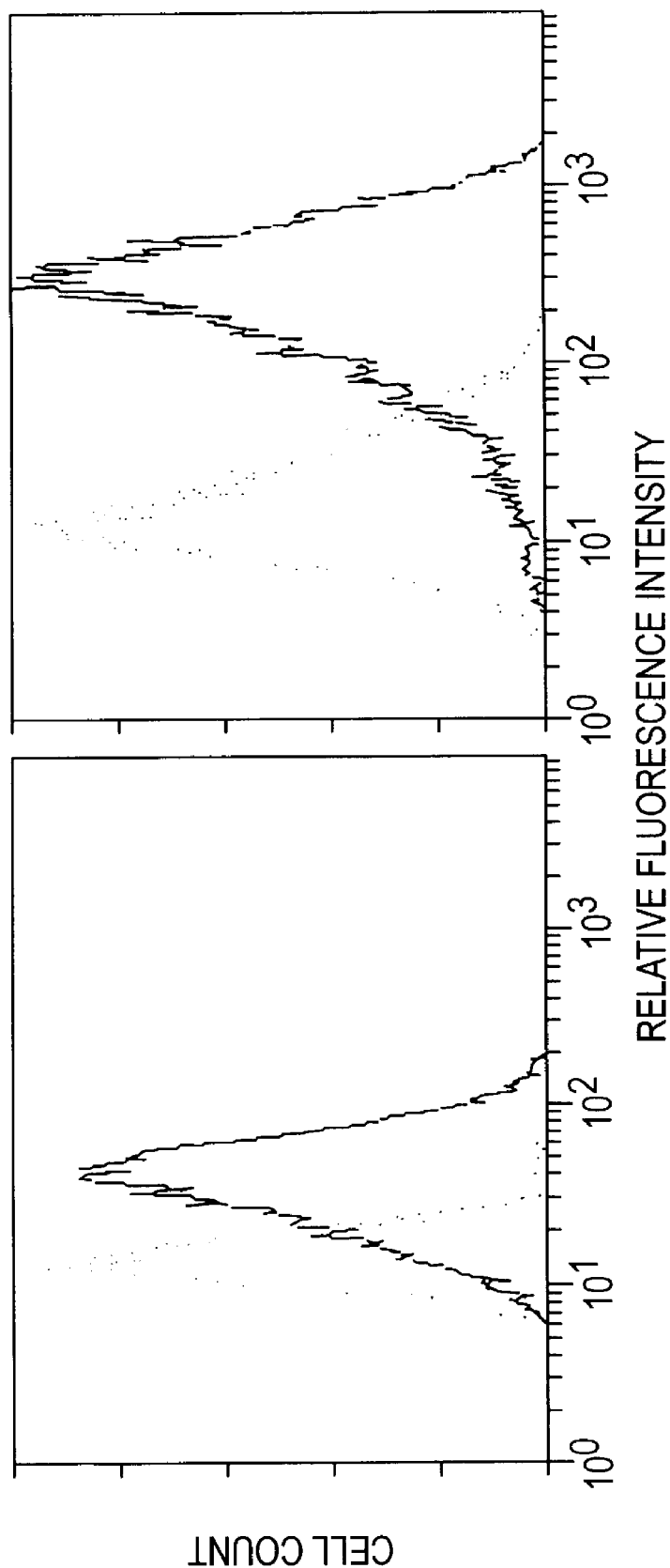

IN SITU RECOMBINANT PCR WITHIN SINGLE CELLS

FIELD OF THE INVENTION

This invention concerns the treatment of cell populations and relates to methods of treating cell populations, e.g. for analysing the linkage of genes within individual cells of a heterogeneous population, novel protein and nucleic acid compositions, and kits for performing said methods.

BACKGROUND OF THE INVENTION

This invention concerns techniques for the treatment of populations of cells, typically heterogeneous populations of cells, and has particular, but not exclusive, application to the treatment of lymphocytes such as those producing antibodies.

Antibodies are present in serum and bind to and help eliminate diverse pathogens such as toxins, bacteria and viruses. They consist of a Y-shaped protein built from two heavy chains and two light chains. Each chain has a modular construction: each light chain consists of two domains, and each heavy chain has at least four domains. The antigen binding site is fashioned by one domain from the heavy chain (VH domain) and one domain from the light chain (VL domain). Indeed small antigen binding fragments can be prepared which consist only of these two domains, either associated non-covalently, or via disulphide bonds or via a peptide linker. The antigen binding domains are more variable in amino acid sequence than the other domains of the antibody, and are therefore termed variable (V) domains in contrast to the constant (C) domains. The constant domains of the antibody are responsible for triggering antibody effector mechanisms such as complement lysis and cell mediated killing.

Antibodies are made by B-lymphocytes in a process of gene rearrangement. During the development of these cells, the genes encoding the variable domains are assembled from genetic elements. In the case of the VH domains there are three elements, the unrearranged VH gene, the D segment and JH-segment. In the case of the VL domains there are two elements, the unrearranged VL (V lambda or V Kappa) gene and the JL (J lambda or J Kappa) segment. Random combination of these gene segments and random combination of the rearranged VH and VL domains generates a large repertoire of diverse antibodies, capable of binding to diverse antigens. The potential diversity is large (primary repertoire in mouse is greater than $10^{10}$), although the repertoire expressed at any time must be less than the total number of lymphocytes (in mouse less than $10^8$)

In the first stage of the immune response, antigen is recognized by lymphocytes and they proliferate and secrete antibody which is usually of low affinity (less than $10^6 M'$).

On further encounter with antigen (as in hyperimmunisation), the V-genes of these cells are subjected to mutation and lymphocytes displaying antibody with enhanced affinity are selected. This process, in which high affinity antibodies are made in two stages from a primary repertoire and subsequently from a hyperimmune repertoire is highly efficient. It has advantages over selecting antibodies in a single step, as this would require a much larger primary repertoire (the potential hyperimmune repertoire is perhaps greater than $10^{30}$)

Traditionally cell lines making high affinity antibodies have been prepared by fusing B-lymphocytes from a hyperimmunised animal with a myeloma cell line. This immortalises the B-lymphocytes and allows the cloning and screening of cells for production of monospecific antibodies binding to antigen. Such monoclonal antibodies have found a wide variety of uses in therapy and diagnostics. However the plasma cells (last stage of differentiation of B-lymphocytes) which are essentially factories for secretion of antibodies, do not fuse. Hence the repertoire of antibody specificities contributed by plasma cells is not accessible by hybridoma technology. This may explain why polyclonal antisera from animals can have higher average affinities than monoclonal antibodies derived from the same animal. There are other disadvantages of hybridoma technology, including the low efficiency of cell fusion, the time consuming steps required to clone hybridomas with the desired antigen binding activities and sometimes the instability of hybridomas.

Recently other methods based on gene technology have been proposed for making antibodies from B-lymphocytes (see Milstein and winter, Nature 349, 293–299 (1991) (reference 11) for review and references). The key step is the cloning of the genes encoding the VH and VL genes directly from B-lymphocytes (or hybridomas) into expression vectors. The genes can be expressed as single variable domains, or Fv or Fab fragments or antibodies in either bacteria or mammalian cells. The key to these recombinant DNA based methods are the rapid cloning of the V-genes directly into expression vectors. This has been achieved by copying and amplifying the V-genes by the polymerase chain reaction (PCR) using "universal" primers which hybridise to the 5' and 3' ends of V-genes. The primers include restriction sites to permit the cloning of the genes directly into expression vectors.

These methods are highly suitable for making antibodies from clones of cells or indeed single lymphocytes. However they do require separate amplification and cloning steps for each single lymphocyte or each individual clone, as the individual VH and VL elements have to be kept together. Alternatively it has been shown that antigen binding activities can be recovered by combining at random VB and VL genes taken from a large repertoire from an immunised animal. This relies on the fact that it may not be necessary to reproduce the precise VH and VL combinations of the B-lymphocyte to recover an antigen-binding activity. Indeed the VH and VL gene combinations derived from a large diverse hyperimmune repertoire will not generally correspond to the original combination of VH and VL genes present in B-lymphocytes. Suppose the VH and VL genes from only one thousand different lymphocytes were reshuffled. It would probably require the screening of over a million VH and VL gene combinations to have a reasonable chance of finding the original VH and VL gene combination from any one cell. This calculation assumes that the VH and VL genes of the chosen cell are unique: this will be particularly true for a hyperimmune response. Thus VH and VL gene combinations selected from a large repertoire of V genes are likely to be artificial combinations. However it is possible that some artificial combinations with binding activities may be similar to the original combination, perhaps with a few amino acid substitutions. Nevertheless it is expected that the majority of such artificial antibodies will have lower affinities than the original combination (although a few may even have improved affinities). To improve their affinities it will generally be necessary to make further steps, for example by recombining one of the chains with a repertoire of diverse partners, or making mutations in the VH and VL genes and to selecting mutants with improved affinity (and thereby mimicking the process of affinity maturation in the hyperimmune response). It would therefore be desirable to clone the correct combinations of VH and VL elements together from heterogeneous and large populations of cells without the need for separate cloning steps for each cell, or without resorting to the entirely random pairing of VH and VL elements. It will also be necessary to clone the original combination of VH and VL genes if it is desired to study the natural antibody response to an antigen.

The present invention is based in part on the proposal that the combination of VH and VL genes present in each cell can be retained if they are copied and the copies of each are linked together preferentially. The linked copies could then be cloned directly into expression vectors. However depending on the efficiency of the linking and copying processes, it might be necessary to first make further copies of the linked genes before cloning.

One way of achieving linkage of the VH and VL genes is by in situ PCR, either of the genes themselves or of cDNA copies of their mRNA transcripts.

The principle of "in-cell" PCR is known and has been disclosed by, for example, Haase et al., 1990 (Proc. Natl. Acad. Sci. USA 87, 4,971–4,975) (reference 15), and by Bagasra et al., 1992 (New Engl. J. Med. 326, 1,385–1,391) (reference 31). However, these papers are concerned with the use of in situ PCR to detect the presence of viral DNA sequences within infected cells. Haase et al. describe a system of PCR using overlapping primers to assemble already adjacent amplified sections of visna virus DNA so as to assemble a complete section of viral genome. However, this is quite distinct from the present invention which involves the realisation that non-contiguous genomic sequences or cDNA may be linked (by PCR) preferentially within the same cell, thus preserving original combinations present within individual cells among a heterogeneous population.

SUMMARY OF THE INVENTION

In a first aspect the invention provides a method of treating a heterogeneous population of cells to link together copies of two or more non-contiguous DNA sequences from at least some of the cells, the arrangement being such that copies of the DNA sequences from an individual cell are preferentially linked in the vicinity of the nucleic acid from which the copies are derived.

The term "preferentially linked" is intended to indicate that those nucleic acid copies derived from a nucleic acid sequence within the same cell are more likely to become associated with each other than with a copy derived from a nucleic acid sequence from a different cell. Thus the original combination of genetic elements present in any one particular cell will tend to be conserved. This preferential linkage occurs in the "vicinity" of the nucleic acid sequence from which the copies are derived. Use of this term is intended to indicate that the preferential linkage defined above occurs relatively locally, near the site of synthesis of the copied nucleic acids. The diameter of a mammalian cell is typically in the range 5–15μm. Since the key factor is preferential linkage between nucleic acids copied from templates within the same cell, the volume or 'vicinity' within which linkage can occur preferentially varies according to the density of sites of nucleic acid synthesis. For reasons described below, such foci or sites need not always be intact cells. The sites of synthesis should however generally be separated by at least one typical cell diameter (5–30 um) because there may be some diffusion of the synthesised nucleic acid copies before linkage occurs. Thus separation or "compartmentalisation" of the sites of synthesis will aid in maintaining the preferential nature of the linkage. These practical constraints require that linkage generally occurs within 30–60 um of the site of synthesis, although as explained above, if the separation of the compartments within which synthesis takes place is increased, the effective volume available for preferential linkage is also increased.

There are two convenient methods of achieving this compartmentalisation, which allows for preferential linkage. One is to perform the reactions within intact or substantially intact cells, and the other is for the reactions to be performed in discrete, physically separated localities.

The gene elements of cells could be encapsulated together and then the individual genes copied and the copies linked together within the capsule. The capsule must be robust enough to survive the copying process and retain the individual gene copies sufficiently to allow linking of the gene copies from the same cell. The capsule can be permeable to reagents, such as oligonucleotide primers and polymerase, or impermeable in which case the reagents must be introduced into the capsule. The capsule could be the nuclear membrane, the plasma membrane or an artificial capsule constructed around the cell. The artificial capsule could be a separate artificial membrane or a different liquid phase, for example an organic solvent. Thus the cell membrane might form the capsule if fixed with formaldehyde and made permeable to reagents.

An example of this is provided by in situ "in-cell" PCR. The general technique of in-cell PCR is known and typically involves fixing (i.e. stabilising with respect to temperature) and permeabilising the cells (so as to allow PCR reagents to enter the cell) and performing PCR in the conventional manner. There may be some diffusion of the PCR products into the external medium. However, in the method of the present invention, these products and excess PCR reagents may be removed by washing.

Alternatively the cells and reagents could be introduced together into droplets and dispersed in an organic phase as an emulsion, in which case it is necessary to ensure that the majority of droplets are occupied on average by a single cell.

As a further possibility, if cells were dispersed away from each other, for example on a surface, such as glass or plastic, or in an inert solid medium, such as agar or silica gel, or in a viscous medium such as glycerol or glucose solutions, there would be limited diffusion (or convection) of the gene copies from one cell to the next. Therefore the gene element of one cell would tend to be linked to the gene element of the same cell, although there might be some linkage to the gene elements of other cells.

Thus in a second aspect, the invention provides a method of treating a population of cells to link together copies of two or more non-contiguous genomic DNA or physically separated cDNA sequences from at least some of the cells, comprising treating the cells to stabilise them with respect to temperature and to permeabilise them with respect to reagents; adding primers for performing the polymerase chain reaction (PCR) such that the primers diffuse into the interior of the cells; subjecting the cells to suitable treatment so the DNA sequences of a particular cell are copied within that cell by PCR; and linking together the copies of DNA sequences within the vicinity of the cell from which they were copied.

The preferential linkage can be brought about by suitable techniques, e.g. by ligation using DNA ligase (with or without prior digestion with restriction enzymes). However, most conveniently, the preferential linkage is brought about by PCR. This may be done by the use of sets of primers where an end of a primer which primes the synthesis of one nucleic acid sequence is complementary to an end of a primer which primes the synthesis of a second nucleic acid sequence.

Preferably the DNA sequence subjected to PCR is derived from cellular mRNA. This is conveniently achieved by reverse transcription of the MRNA.

The use of fluorescently labelled PCR primers allows for the analysis of a population of cells for example by counting cells which express a particular gene or combination of genes.

Thus, in a further aspect the invention provides a method of treating a population of cells, comprising treating the cells to stabilise them with respect to temperature and to permeabilise them with respect to reagents; adding fluorescently labelled primers for performing PCR, such that the primers diffuse into the interior of the cells; subjecting the cells to suitable treatment so the nucleic acid sequences of a particular cell are copied by PCR; and monitoring the fluorescent labels.

A further aspect provides a method of treating a population of cells, comprising treating the cells to stabilise them with respect to temperature and to permeabilise them with respect to reagents; adding primers for performing PCR, such that the primers diffuse into the interior of the cells; subjecting the cells to suitable treatment so DNA sequences of a particular cell are copied within that cell by PCR; adding fluorescently labelled probes; and monitoring the fluorescent labels.

Typically a cell population subjected to this method of treatment is suitable for analysis by fluorescence activated cell sorting (FACS).

Fluorescence labelling of amplified DNA is particularly advantageous, as it can allow for the sorting of labelled cells (e.g. by FACS) and the direct cloning of the amplified DNA from sorted cells.

Conveniently, two different primers labelled with different fluorescent labels are employed. This can allow for the analysis of two different sub-populations within a heterogeneous population in one experiment. Typically, fluorescent labelling allows for counting of labelled cells, which is a preferred feature of this aspect of the invention.

Conveniently, cells may be stabilised with respect to heat by 'fixing' with formaldehyde. A convenient method of permeabilising cells is to treat them with a detergent, typically the non-ionic detergent Nonidet P40 (NP40).

It may be desirable that the methods defined above further comprise one or more rounds or further rounds of PCR. Preferably any further rounds of PCR are performed using "nested" primers, which are complementary to sequences copied in the preliminary amplification.

A washing step may be usefully incorporated after the linkage step into any of the methods defined above, particularly those using in-cell PCR, to remove from the external surface or outer layers of cells unwanted material, e.g. linked copies from other cells, in order to reduce the background "noise". This is particularly useful if one or more further rounds of PCR are to be performed.

Any of the methods defined thus far are particularly suitable for application to the study of immunoglobulin VH and VL domains. Conveniently, therefore the nucleic acid sequences copied may be genomic DNA sequences (such as those encoding immunoglobulin VH and VL domains). However, due to the higher effective concentration of MRNA (relative to genomic DNA) in a cell actively expressing a particular protein, it is preferable that mRNA may be reverse transcribed in situ into cDNA and the resulting cDNA amplified by in cell PCR. Further, analysis of mRNA rather than genomic DNA more accurately reflects the activity of the cell.

The various method aspects of the present invention are also readily applicable to the study of the T cell receptor (TCR) V-genes in populations of cells.

Clearly, it may be beneficial to isolate the nucleic acid produced by the method aspects of the invention. Thus the products are typically inserted into suitable vectors. The inserted nucleic acid product is then generally sequenced or annealed to nucleic acid probes to confirm its identity. Particularly suitable are vectors which may express the nucleic acid sequence as a polypeptide. This is of special interest when isolating sequences encoding VH and/or VL domains, as it represents a method of producing monospecific antibody binding fragments. Such cloning and expression vectors are well known to those skilled in the art. Particularly preferred is the technique whereby VH/VL combinations are expressed on the surface of a phage (McCafferty et al. (9)), such a technique representing a powerful selection method.

Expression on the surface of a phage is a particular embodiment of a generally preferred feature: expression of the cloned nucleic acid product as a fusion protein. As an alternative to fusion with the coat protein of a phage, the cloned nucleic acid product could be expressed as a fusion protein with a peptide tag for detection purposes.

Thus the invention extends to proteins expressed by means of the method aspects of the invention.

In a further aspect the invention provides a composition comprising copies of two or more nucelic acid sequences preferentially linked in the vicinity of the nucleic acid sequences from which the copies were derived.

In another aspect, the invention provides a kit for performing any of the method aspects of the invention, comprising at last a PCR primer for copying a DNA sequence of interest and intructions for use.

Optional components which may be included in the kit include further overlapping and/or nested PCR primers, labelled oligonucleotides which may be used as PCR primers or as probes, other PCR reagents (such as Taq polymerase, buffers) or reagents for fixing and permeabilising cells.

It will be apparent that the methods of the invention have a wide variety of potential applications. Normally, one would expect to employ such methods on heterogeneous populations of cells, but there is no reason why the method should not be used on a uniform population if it would reveal information of interest. These applications include the construction of monoclonal antibodies (or fragments thereof) from populations of a B-lymphocytes, but it is by no means limited to this application. For example, it might be used for analysis of the combinations of chromosomes present in populations of somatic cell hybrids. Alternatively, instead of analysing diploid cell populations the method could be used to study haploid cell populations, such as sperm cells. Thus the method could be employed to investigate, for example, linkage between genetic markers in human sperm, in a manner which improves upon that described by Li et al. (1988, Nature 345, 414–417) (reference 39), as will be apparent to those skilled in the art.

BRIEF DESCRIPTION OF THE DRAWINGS

The invention will be better understood by reference to the following illustrative examples and by reference to the accompanying drawings, in which:

FIGS. 2 A–B to 5A–B show DNA sequences of oligonucleotides used as primers in Example 1 SEQ ID NO:60 to SEQ ID NO: 67 and SEQ ID NOS:1–10, 34, 35, 69 and 70;

FIG. 9A–B illustrate flow cytometry of K562 cells with bcr-abl amplified in accordance with a method of the invention.

EXAMPLE 1

Linking of VH and VL genes from cells fixed with formaldehyde

Figure 1:
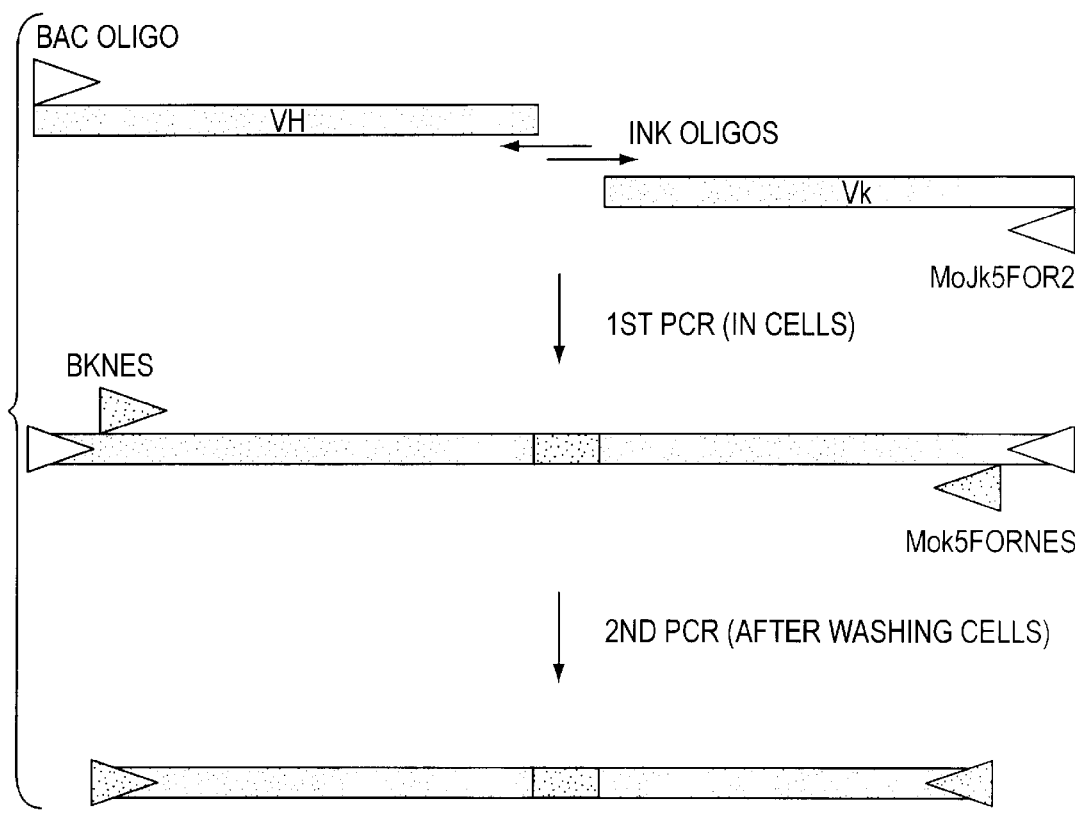
FIG. 1 illustrates schematically certain steps of a method in accordance with the invention.
Figure 4B:

The VH and VL genes of a hybridoma cell line can be copied using the polymerase chain reaction and primers located at the 5' and 3' end of the VH and also of the Vk gene (FIG. 1). The amplified VH and Vk DNA are also linked during the PCR reaction, in the order 5' VH-Vk 3' by virtue of a match between the primers at the 3' end of the VH gene, and the 5' end of the Vk gene (Stage 1). To fish out the linked species from the unlinked species, a second set of 'nested' PCR primers is used (Stage 2).

The VH and Vk genes are linked preferentially within the same cell as follows. The cell is first fixed with formaldehyde to stabilise it to the temperature cycling, and treated with Nonidet P40 to permeabilise the cell clones analysed by probing and sequencing.

The nucleotide sequences of the mature heavy chain VH domains and the Vk light chain genes of the antiphenyloxazolone hybridomas NQ2/12.4 and NQ10/12.5, and the encoded protein sequences, are given in FIGS. 2A–B to 5A–B. In FIGS. 2A–B and 4A–B, the VH and Vk genes are linked by a nucleotide sequence encoding a polypeptide spacer providing a flexible polypeptide chain to link the two domains. Thus the complete nucleotide sequence in FIGS. 2A–B and 4A–B encodes a single chain Fv fragment. The spacer is incorporated within the PCR primers MoVhlnk3 and MoVklnk3, which are used with a VH back (NQ10/12.5 or NQ2/12.4) primer and a Vk forward primer (MoJkFOR2) to amplify and link the VH and Vk genes in a form suitable for expression. FIGS. 3A–B and 5A–B are similar, and show a shorter linker that contains a unique restriction site to allow the cloning of a longer polypeptide linker by introducing a synthetic oligonucleotide. To identify the linked genes, further cycles of PCR are used with a nested VH back (NQ10/12.5BKNES or NQ2/12.4BKNES) primer and a nested Vk forward (MokFORNES) primer. In the example below, the sequence of the hybridoma genes was already known and primers specific to the hybridomas were designed. However in principle more general primers could be used, for example, to clone variable domains in general by PCR (reference 5). Also the second round of PCR amplification in the example gives rise to a single chain Fv truncated at both N- and C-terminus. However, a different set of primers should overcome these problems. For example, for the first stage PCR amplification-assembly, a family of Vk forward primers might be designed directly to the 3' side of the J-regions, either in the C kappa or C lambda constant domain for RNA templates, or in the region of DNA next to the splice junction for genomic DNA templates. Linking primers would be used that encoded a polypeptide sequence (as above), for example to join the VH and Vk as a single chain Fv fragment. The Vh back primer would incorporate a restriction site for cloning into expression vectors. For the second stage amplification of the linked VH and Vk genes, Vk forward primer(s) based within the Jk region itself (and incorporating restriction site for cloning into expression vectors) might be used in conjunction with the VH back primer.

Preparation of cell templates

NQ2/12.4 or NQ10/12.5 hybridoma cells were grown in tissue culture flasks in Dulbecco's modified Eagle's medium containing 5% foetal bovine serum. Cultures in late logarithmic growth phase were harvested by rinsing adherent cells into the supernatant medium, and centrifuging the medium at 800 rpm for 5 minutes at room temperature. The supernatant was removed and the cells were resuspended in 5 ml phosphate buffered saline (PBS, pH 7.2) at room temperature and again centrifuged at 800 rpm for 5 mins (1st wash). Two further washes in 5Sil PBS were given under the same conditions. The cell pellets were then suspended in 10% formal saline (10% formalin [i.e. 4% formaldehyde] and 0.15M NaCl in distilled water), using 1 ml per 10–50ml of original culture, and transferred to 2 ml Eppendorf Safe-Lock tubes. They were incubated on ice for 1 hour, with frequent agitation on a vortex mixer. The cells were then spun down at 13,000 rpm in a microfuge, and washed 3 times with 1ml ice-cold PBS, dispersing them by pipetting up and down several times at each wash. Following removal of the PBS after the 3rd wash, the pellets were resuspended in 1ml ice-cold Nonidet P40 in water, and incubated on ice for a further 1 hour with frequent agitation. The cells were washed 4 more times in 1 ml ice-cold PBS, with vigorous pipetting, and suspended in 0.2–0.5 ml cold PBS containing 0.1M glycine. A sample was examined microscopically in a haemocytometer, and if clumps were present they were dispersed into single cells by vigorous pipetting or repeated passage through a 26 gauge hypodermic needle. The cells were then counted and adjusted to $10^7$ per ml in PBS +0.1M glycine, and aliquoted into 0.5 ml tubes (usually 0.05–0.1 ml per tube) and frozen in dry ice. The frozen aliquots were stored at −70 degrees C.

Assembly and Amplification

Heavy and light chain variable regions were assembled and amplified by a 2-stage Polymerase Chain Reaction. In the first stage, VH and Vk genes were linked together, and in the second stage the assembled product was amplified from the cell template. Reactions were carried out in Techne HI-TEMP 96 polycarbonate microplates using a Techne PHC-3 programmable heating block, or in 0.5 ml Sarstedt tubes using a BioTherm Inc. BioOven.

Reaction conditions were as follows:

1ST STAGE:

| | |
|---|---|
| Water | 26.5 ul |
| Forward Vk primer | 2.5 ul |
| Back Vh primer | 2.5 ul |
| Forward Link primer | 0.5 ul |
| Back Link primer | 0.5 ul |
| dNTPs (5 mM) | 2.0 ul |
| 10 × PCR buffer | 5.0 ul |
| Cell template (in PBS/glycine) | 10.0 ul |
| Taq polymerase (5 units/ul) | 0.5 ul |

A drop of oil was added when Techne plates were used, but none when tubes were used in the BioOven. Cycling times and temperatures were as follows:

| Techne PHC-3 Block: | 94° C. | 30 secs | |
|---|---|---|---|
| | 65° C. | 1 min | |
| | 72° C. | 1 min | 30 cycles |
| BioOven: | 95° C. | 30 secs | |
| | 65° C. | 30 secs | |
| | 72° C. | 30 secs | 30 cycles |

1st stage Primers (10 pmol/ul)

V$_h$Back NQ2/12.4 BACK (SEQ. ID NO: 1)
5'CAG GTG CAG CTG AAG GAG TCA GG 3'
OR NQ10/12.5 BACK (SEQ. ID NO: 2)
5'TGC AGC TGG TGG AGT CTG GGG G 3'
V$_K$Forward MoJk5FOR2' (SEQ. ID NO: 3)
5'CTT ACG TTT CAG CTC CAG CTT GG 3'
Forward Link MoVhlnk3 (SEQ. ID NO: 4)
5'CCA CTG CCG CCA CCA CCG CTA CCA CCA
CCA CCT GCA GAG ACA GTG ACC AG 3'
OR MoVhLNK4 (SEQ. ID NO: 5)
5'CAA TTT Ggc tag cTG CAG AGA CAG TGA (Nhe I)
CCA GAG TCC CTT GGC CCC A 3'
Back link MoVklnk3 (SEQ ID NO: 6)
5'GCG GTG GTG GCG GCA GTG GCG GCG GCG
GCT CTC AAA TTG TTC TCA CCC AGT CTC CAG C 3'
OR MoVkLNK4 (SEQ. ID NO: 7)
5'CAG TGT CTC TGC gct agc cCA AAT TGT TCT
CAC CCA GTC TCC AG 3'

(The lnk3 primers were used a a pair, and likewise the LNK4 primers.)

CCA GAG TCC CTT GGC CCC A 3' (SEQ ID NO: 68)
Back link MoVklnk3
5'GCG GTG GTG GCG GCA GTG GCG GCG GCG
GCT CTC AAA TTG TTC TCA CCC AGT CTC CAG C 3' (SEQ ID NO: 6)
OR MoVkLNK4
5'CAG TGT CTC TGC gct agc cCA AAT TGT TCT
CAC CCA GTC TCC AG 3' (SEQ ID NO: 7)

(The lnk3 primers were used as a pair, and likewise the LNK4 primers.) After termination of the first stage, the cell templates were separated from the rest of the reagents and washed. In Techne plates, the supernatant PCR mix and overlying oil were carefully pipetted away, leaving the cells at the bottom of the well. The cells were then suspended in 0.2 ml of PBS/0.1M glycine and spun down in a microfuge at 13,000 rpm. After resuspension in the same buffer they were again spun down for a 2nd wash, then resuspended in 10 μl PBS/glycine for use as the 2nd stage template. Tubes from the BioOven were spun at 13,000 rpm and the supernatant PCR mix removed, and the cells washed twice in 0.2 ml PBS/glycine, before final resuspension in 10 ul PBS/glycine for use as 2nd stage template. All 1st PCR supernatant were saved.

2ND STAGE

| Water | 27.5 ul |
|---|---|
| Forward nested primer (10 pmole/ul) | 2.5 ul |
| Back nested primer | 2.5 ul |
| dNTPs (5 mM) | 2.0 ul |
| 10 x PCR buffer | 5.0 ul |
| Washed stage 1 cell template | 10.0 ul |
| Taq polymerase (5 units/ul) | 0.5 ul |

Cycling conditions were as in the 1st stage reaction, but included a final 10 minutes at 605 degrees.

2nd stage Primers (10 pmol/ul)

Forward nested primer Mok5FORNES (SEQ ID NO: 8)
5'CCC AGC ACC GAA CGT GAG TGG 3'
Back nested primer NQ2/12.4BKNES (SEQ ID NO: 9)
5'CGC CCT CAC AGA GCC TGT CCA 3'
OR NQ10/12.5BKNES (SEQ ID NO: 10)
5'AGC CTG GAG GGT CCC GGA AAC 3'

(used with respective cell template).

The products of both the 1st and 2nd stage PCRs were run in a 2% agarose gel, prepared in 0.5×TBE buffer and containing 0.5 ug/ml ethidium bromide, using phiX174 HaeIII as a marker. The results indicated that in the first stage PCR, fragments of the size expected For single VH and Vk genes are seen, but after the second stage PCR fragments corresponding to the assembled fragments are seen, according to the schematic of FIG. 1.

The putative sequences of the linked fragments are shown in FIGS. 2A–B to 5A–B.

EXAMPLE 2
Use of an emulsion for PCR amplification

In this example, we show that it is possible to make a water in oil emulsion that is stable throughout the PCR cycle, and in which it is possible to amplify plasmid DNA.

After trying a range of detergents, with HLB (Hydrophilic Liphophilic Balance) of 3.5–6 (from Triton-X15 to Brij52), and a range of oils (n-dodecane to heavy mineral oil (Sigma)), we found that Span-60 (Sigma) and light white oil (Sigma) gave an emulsion which survived at least 30 rounds of PCR cycling. Droplet size was estimated as 25–50 um diameter sufficient to contain a cell. Conditions suitable for PCR in emulsions are given below. The sequences of the primers are given in Example 1.

| 5 ul | 10 × PCR buffer [10 × PCR = 100 mm Tris-HCl pH 8.3/500 mM, KCl/25 mM MgCl$_2$] |
|---|---|
| 4 ul | 2.5 mM deoxynucleotide triphosphates (pH 7.5) |
| 2 ul | NQ10/12.5 BACK primer (10 pmoles/ul) |
| 2 ul | MoJkSFOR2 primer (10 pmoles/ul) |
| 2 ul | MoVHLNK4 (1 pmole/ul) |
| 2 ul | MoVkLNK4 (1 pmole/ul) |
| 5 ul | Taq DNA Polymerase (Cetus 5 U/ul) |
| 1 ul | plasmid containing NQ10/12.5 VH gene (3 ng pBluescriptIIKS from Stratagene) |
| 1 ul | plasmid containing NQ10/12.5 Vk gene (3 ng pBluescriptIIKS from Stratagene) |
| | H$_2$O (HPLC grade) to 50 ul |

The mixture was incubated for 5 minutes at 64° C.
100 ul freshly made 2% Span 60 in Light White Oil was added at 64° C. The two phases were mixed by vortexing vigorously for 30 seconds then immediately transferred to the PCR block (Techne PHC-3) at 64° C. and subjected to 30 cycles of 94 deg. C. 1 min, 62° C. C. 1 min, 72 deg. C. 2 min, then held at 64° C. The emulsion was checked visually and appeared to be stable but had creamed. The excess oil phase was removed and remaining oil and Span 60 removed by one extraction at 64° C. with diethyl ether, and then two further extractions at room temperature. The tubes were incubated at 64° C. to evaporate the excess ether and 1 ul of the DNA was then removed for a second round of PCR with the nested primers as in Example 1. Analysis of the DNA on a 2% high-gelling temperature agarose gel demonstrated that assembly had occurred.

It is helpful to protect the Taq polymerase from denaturation that occurs in the microdroplets or in the formation of the droplets. Thus we have discovered the yields of assembled genes can be improved by using encapsulated enzyme, for example by using *E. coli* bacteria in which the enzyme has been cloned and is expressed (Engelke et al., Anal Biochem. 191, 396–400 (1990) (reference 40). By making alterations in the protocol above, within the skills of someone skilled in the art, it is to be expected that the VH and Vk genes could be amplified and assembled from populations of cells.

EXAMPLE 3

Reverse transcription of mRNA and amplification of cDNA.

Monoclonal antibodies have provided reagents for the identification of marker proteins (and lipids and carbohydrates) expressed within cells (1), on the surface of cells (2) or secreted from cells (3). These reagents have had diverse uses, ranging from the localisation of cells in histological sections (1) to the use of fluorescence activated cell sorting (FACS) of populations of cells (4). However given the nucleotide sequence encoding a desired marker, we could in principle use the mRNA species as a marker for a cell. We have therefore explored a process in which the mRNA is reverse transcribed within the cell, the cDNA is amplified using the polymerase chain reaction and is detected in the cell using fluorescent PCR primers.

In principle such a process could also be used to detect and to clone combinations of mRNAs by linking the PCR amplified cDNAs within the same cell. In particular it could help in the cloning of Ig V-gene combinations from immunised or auto-immune sources using recombinant DNA techniques. At present, repertoires of antibody heavy and light chains are prepared from lymphocyte populations by PCR (5,6,7), combined at random (8) and expressed as soluble fragments in bacteria for screening with antigen (8), or displayed on the surface of filamentous phage and selected by panning (9,10). However the original combinations of heavy and light chains of the B-lymphocytes are destroyed (11,12), and the artificial combinations can be dominated by promiscuous chains (10,13), leading to different affinities (10) and specificities (14). In-cell PCR and linkage of heavy and light chains would allow the original combinations of the B-lymphocytes to be retained.

Earlier work had shown that lentivirus DNA can be amplified in situ using PCR, and the infected cells detected by autoradiography (15). We have developed a similar approach to making and amplifying cDNAs within the same cell, as demonstrated with two hybridoma cell lines, B1-8 (16) and NQ10/12.5 (17), and the K562 erythroleukaemia line (18). The cells were fixed with formalin and permeabilised with the detergent NP40 to allow the access of nucleotides, primers and enzymes. For linking of the Ig heavy and light chain V-genes of the same cell during in-cell PCR, one primer was designed to prime at the 3' end of the VH gene, and another at the 5' end of the VL gene, but with complementary tails to allow the self-assembly of the VH and VL genes.

Cell lines

NQ10/12.5 murine hybridoma cells were grown in Dulbecco's modified Eagle's medium supplemented with 5% fetal bovine serum (FBS), and B1-8 hybridoma cells in RPMI 1640 medium supplemented with 5% FBS. Cells were used or passaged at late log phase, when almost all were viable. NQ10/12.5 secretes a kappa light chain and B1-8 a lambda light chain (16,17). The sequences of the VH and VL genes for both these hybridomas are known (16,17). The human myeloid leukemia cell line K562 was grown in RPMI with 5% FBS. This line carries the Philadelphia chromosome, which is characterised by a bcr-abl fusion gene as a result of a translocation between the abl proto-oncogene on chromosome 9 and the bcr gene on chromosome 22 (19).

Cell fixation and permeabilisation

Cells ($10^7$ to $10^8$) were sedimented at 50×g for 5 mins, washed 3 times in 5 ml PBS pH 7.2 at room temperature then suspended in 1 ml ice-cold 10% formaldehyde solution in 0.15M NaCl (formal saline). They were kept on ice for 1 hour, with occasional agitation on a vortex mixer. They were then spun at 13,000 rpm in a microcentrifuge for 2.5 mins and washed 3 times in ice-cold PBS, with vigorous pipetting with a Pasteur pipette to resuspend and disperse any clumps visible by eye. The cells were next suspended in 0.5% Nonidet P40 (NP40, B.D.H.) in water. After a further 1 hour incubation on ice with frequent agitation, they were again washed 3 times in ice-cold PBS with vigorous pipetting. A final wash was given in PBS containing 0.1M glycine, and the cells were resuspended in 0.2 to 0.5 ml of the same buffer, using a 1 ml syringe and 26 gauge needle to disperse the clumps visible using a light microscope. The cells were counted, and for most experiments adjusted to a final concentration of $10^7$ per ml. They were frozen in small aliquots in dry ice and stored at −7° C. for up to a month.

Oligonucleotides

The oligonucleotides are listed according to their use as primers or probes. The sequences were based on the sequence of the hybridoma V genes (16,17), and the bcr-abl gene (20), and were synthesised using an Applied Biosystems 394 DNA synthesiser and used without purification.

cDNA synthesis
MOLFOR (SEQ ID NO: 11) (5' CTT ACG TTT CAG CTC CAG CTT GG 3'), MOJH3FOR (SEQ ID NO: 12) (5' TAG GAC TCA CCT GCA GAG ACA GTG 3'), B1-8LFOR (SEQ ID NO: 13) (5' GCC TAG GAC AGT CAG TTT GGT TC 3'), B1-8VHLINK3 (SEQ ID NO: 14) (5' CCA CTG CCG CCA CCA CCG CTA CCA CCA CTG AGG AGA CTG TGA GAG TGG TGC 3').
first PCR
MOLFOR, MOJH3FOR, B1-8LFOR, B1-8VHLINK3, NQ2BK (SEQ ID NO: 15) (5' CAG GTG CAG CTG AAG GAG TCA GG 3'), NO10BK (SEQ ID NO: 16) (5' TGC AGC TGG TGG AGT CTG GGG G 3'), B1-8BK (SEQ ID NO: 17) (5' CAG GTC CAA CTG CAG CAG CCT G 3'), BCR1A (SEQ ID NO: 18) (5' ACT TAC ACG TTC CTG ATC TC 3'), ABL2C (SEQ ID NO: 19) (5' TTA TCT CCA CTG GCC ACA AA 3'), MOVHLINK3 (SEQ ID NO: 4) (5' CCA CTG CCG CCA CCA CCG CTA CCA CCA CCT GCA GAG ACA GTG ACC AG 3'), MOVKLINK3 (SEQ ID NO: 6) (5' GCG GTG GTG GCG GCA GTG GCG GCG GCG GCT CTC AAA TTG TTC TCA CCC AGT CTC CAG C 3'), B1-8VLLINK3 (SEQ ID NO: 20) (5' GCG GTG GTG GCG GCA GTG GCG GCG GCG GCT CTC AGG CTG TTG TGA CTC AGG AAT CTG C 3').
first PCR linker primers:
B1-8VLLINK3, B1-8VHLINK3, MOVHLINK3, MOVLLINK3.
Second PCR (nested primers):

-continued

NQ16BKNES (SEQ ID NO: 10) (5' AGC CTG GAG GGT CCC GGA AAC 3'), B1-8BKNES (SEQ ID NO: 21)
(5' GAG CTT GTG AAG CCT GGG GCT T 3'), MOLFORNES (SEQ ID NO: 22) (5' CCC
AGC ACC GAA CGT GAG TGG 3'), B1-8FORNES (SEQ ID NO: 23) (5' CCA CCG AAC
ACC CAA TGG TTG CT 3'), V186.2 (SEQ ID NO: 24) (5' AGA CAA ACC CTC CAG
3').
Second PCR (nested) tagged primers for fluorescence
labelling:
M13B1-8BKNES (SEQ ID NO: 25) (5' CAG GAA ACA GCT ATG ACC GAG CTT GTG AAG
CCT GGG GCT 3'), M13B1-8FORNES (SEQ ID NO: 26) (5' CAG GAA ACA GCT ATG ACC
CCA CCG AAC ACC CAA TGG TTG CT 3'), -21MOLFORNES (SEQ ID NO: 27) (5'TGT
AAA ACG ACG GCC AGT CCC AGC ACC GAA CGT GAG TGG 3'), -
21NQ10BKNES (SEQ ID NO: 28) (5' TGT AAA ACG ACG GCC AGT ACG CTG GAG GGT
CCC GGA AAC 3'), -21BCR1B (SEQ ID NO: 29) (5' TGT AAA ACG ACG GCC AGT TCT
GAC TAT GAG CGT GCA GA 3'), -21ABL2D (SEQ ID NO: 30) (5' TGT AAA ACG ACG
GCC AGT AGT GCA ACG AAA AGG TTG GG 3').
Third PCR fluorescent primers:
-21R0X or -21FAM (SEQ ID NO: 31) (5' TGT AAA ACG ACG GCC CAG 3'), M13ROX (SEQ ID NO: 32)
(5' CAG GAA ACA GCT ATG AC 3') were obtained commercially
from Applied Biosystems.
Probes:
B1-8LPRB (SEQ ID NO: 33) (5' CTG TAC CAT AGA.GCA CAG 3'), NQ10PRB (SEQ ID NO: 34) (5' GAG
TTT CCG GGA CCC TCC AG 3'), NQ10KPRB (SEQ ID NO: 35) (5' TTG GAA CCA GTT
CAT GTA C 3'), V186.2.

cDNA

For in-cell CDNA synthesis of Ig V-genes of the hybridomas, $10^6$ fixed cells were thawed, spun down and washed in 200 ul water, then resuspended in 20 ul water. A 'first strand mix' was freshly prepared, comprising 5 ul 10×1st strand buffer (1.4M KCl, 0.5M Tris-HCl pH8.1 at 42° C., 80 mM $MgCl_2$), 5 ul 0.1M dithiothreitol (DTT), 5 ul 5 mM dNTPs, 25 pmol each forward primer, 80 units RNase inhibitor (RNasin, Promega) and water to a total volume of 28 ul. The cells were heated to 65° C. for 3 mins then cooled on ice. The 'first strand mix' was added, followed by 40 units Super RT AMV reverse transcriptase (HT Biotechnology Ltd., Cambridge). The cells and reagents were mixed and incubated at 42° C. for 1 hour, then the cells were spun down, washed in 200 ul PBS (pH 7.2) containing 0.1M glycine (PBS/0.1M glycine) and resuspended in 20 ul of the same buffer for use immediately in PCR. For K562 cells, cDNA synthesis was as above except using random primers and oligo (dT) (21).

For cDNA synthesis from hybridoma cell lysates, viable cells ($5×10^6$) were boiled for 5 mins in 100 ul water containing 0.1% diethyl pyrocarbonate and spun for 2 mins at 13,000 rpm in a microcentrifuge. A 'first strand mix' was prepared, comprising 10 ul 10×1st strand buffer, 5 ul 5 mM dNTPs, 5 ul 100 mM DTT, and 25 pmol each forward primer. It was added to a volume of 62–67 ul supernatant from the boiled cells, and the mixture heated at 65° C. for 3 mins and left to cool at room temperature for 15 mins. RNasin (160 units) and reverse transcriptase (100 units) were added to bring the total volume to 100 ul, followed by 1 hour incubation at 42° C. For PCR amplification, the reactions were set up as below, except with 5 ul of the soluble template per tube.

In-cell PCR from CDNA

Reactions were set up in 50 ul volumes in 0.5 ml Sarstedt tubes with 10 ul fixed template cells in PBS/0.1 M glycine buffer, 25 pmol back primer, 25 pmol forward primer, 200 uM dNTPs, 5 ul 10× Taq polymerase buffer (Promega) and 2.5 units of Taq polymerase. The tubes were subjected to up to 40 cycles of PCR with denaturation at 95° C. and extension at 72° C. for 1 min each. Annealing was for 1 min at temperatures ranging from 60° C. to 72° C. For situations requiring cell recovery, a thermal cycling oven ("BioOven", BioTherm Corp.) was used, which did not require the use of a mineral oil overlay. Where cell recovery was not required, cycling was performed on a cycling heat block (Techne PHC-3) with an overlay of 50 ul mineral oil.

In-cell PCR and assembly from CDNA

Figure 6:
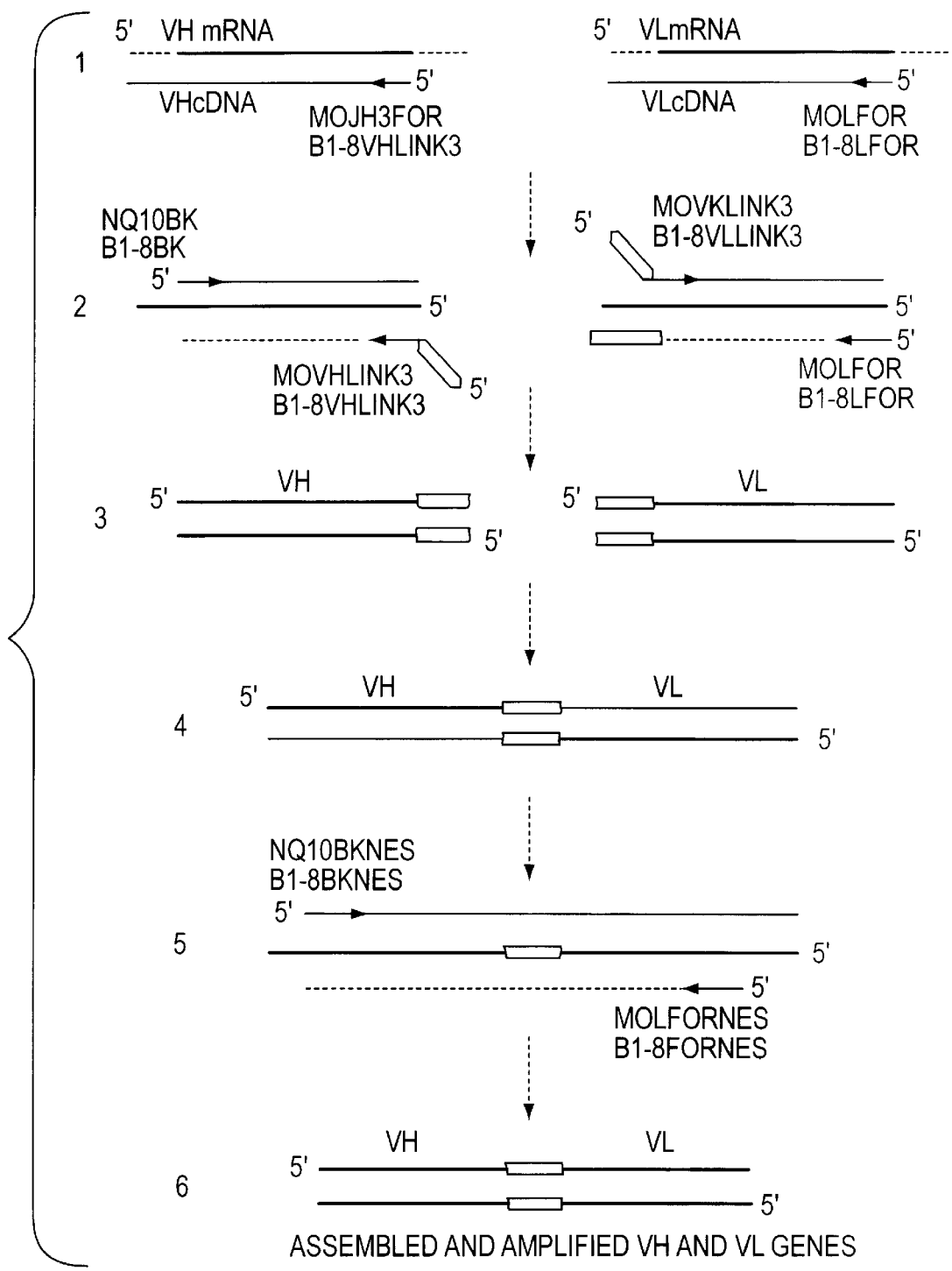
FIG. 6 illustrates schematically assembly and nested amplification of Ig V-genes from hybridomas for cloning.

The cDNAs were amplified by PCR and linked in the same reaction by using primers with complementary tails (22) (FIG. 6).

FIG. 6 illustrates assembly and nested amplification of Ig V-genes from hybridomas for cloning, cDNA synthesis and assembly of VH and VL gene from hybridomas NQ10/12.5 and B1.8. Sequences of primers (small arrows) indicated are as described previously. In each step the template strand is marked with a thick line, and the newly synthesised (first) strand with a thin line; in some cases, two steps are combined in the figure, and the second synthesised strand (using the first as template) is then marked with a dashed line. Sequence tags for assembly are marked as blocks. (1) cDNA synthesis (2) first PCR, (3) further rounds of first PCR giving rise to VH and VL with "tagged" and complementary ends, (4) assembly during first PCR of VH and VL, (5) second "nested" PCR, (6) assembled and amplified VH and VL genes. Note that for the cDNA synthesis from B1-8 cells, the tagged primer B1-8VHLINK3 was used, but the tag is not marked on the figure.

Reactions were set up in 50 ul volumes in tubes as follows:

25 pmol VH back primer, 25 pmol VL forward primer, 10 pmol VH forward primer with linker sequence, 10 pmol VL back primer with linker sequence, 200 uM dNTPs, 5 ul 10×Taq polymerase buffer, 2.5 units Taq polymerase, and 10 ul fixed cells in PBS/0.1M glycine buffer. Generally 10 (but sometimes up to $5×10^5$) cells per tube were used, and the tubes were given 30 cycles of 95° C. for 30 secs, 65° C. for 30 secs and 72° C. for 30 secs. The cells were spun down at 13,000 rpm, washed twice in 200 ul PBS/0.1M glycine, and resuspended in 10 ul PBS/glycine. To amplify the assembled products, a second PCR was set up with the washed cells, nested primers (23) using 25 pmol nested VH back primer and 25 pmol nested VL forward primer, 200 uM dNTPs, 5 ul 10×PCR buffer and 2.5 units Taq polymerase. The cells were subjected to 30 more cycles of PCR, and DNA for cloning was isolated from the supernatant.

In experiments involving a mixture of two cell lines, all four PCR primers for each cell line (a total of eight primers) were included in both first and second "nested" PCRs using a 100 ul reaction volume. cDNA was synthesised from a 1:1 mix of B1-8 and NQ10/12.5 (NQ10) fixed cells using the primers MOLFOR, MOJH3FOR, B1-8LFOR and B1-8VHLINK3, and the cells washed and resuspended in PBS/0.1 M glycine for PCR assembly. The first PCR was carried out using the VL forward primers MOLFOR and B1-8LFOR and the VH back primers NQ10BK and B1-8BK. To link the two sets of genes, the PCR linker primers MOVHLINK3, MOVKLINK3, B1-8VLLINK3 and B1-SVHLINK3 were also included. The 3' ends of the PCR linker primers are complementary to the ends of the DNA template, but incorporate a 5' "tag" to allow assembly of the VH and VL genes (FIG. 6). The tags were identical for both NQ10 and B1-8 linker primers, so that all possible combinations of VH and VL could be formed. The second PCR used the nested primers NQ10BKNES, MOLFORNES, B1-8BKNES and B1-8FORNES. Fluorescence detection of intracellular PCR products cDNA in the B1-8 and NQ10 cells was subjected to PCR to amplify VH genes, using the primers indicated in Table 1. They were then washed twice and the genes further amplified with nested PCR primers tagged with sequences complementary to those fluorescence tagged primers −21FAM, M13ROX used for DNA sequencing) (Table 1). After washing, a third PCR was used with 3 pmol of M13 or −21 primers labelled with 6 carboxy-X-rhodamine (ROX) (Applied Biosystems). Conditions for each PCR were 94° C. for 40 secs, 58° C. for 40 secs, and 72° C. for 40 secs. After the final stage the cells were washed three times in TE buffer (10 mM Tris-HCl, 1 mM EDTA, pH 7.4) and suspended in the same buffer. A similar protocol was used to amplify assembled VH-VL DNA (Table 1). the cDNA of K562 cells was subjected to amplification using PCR primers specific for the bcr-abl fusion gene (Table 1). For fluorescence microscopy of K562, ROX labelled primers were used in the third PCR, and for flow cytometry both ROX and 5'-carboxyfluorescein (FAM) labelled primers (Applied Biosystems) were used in separate preparations (FIG. 7).

Figure 7:
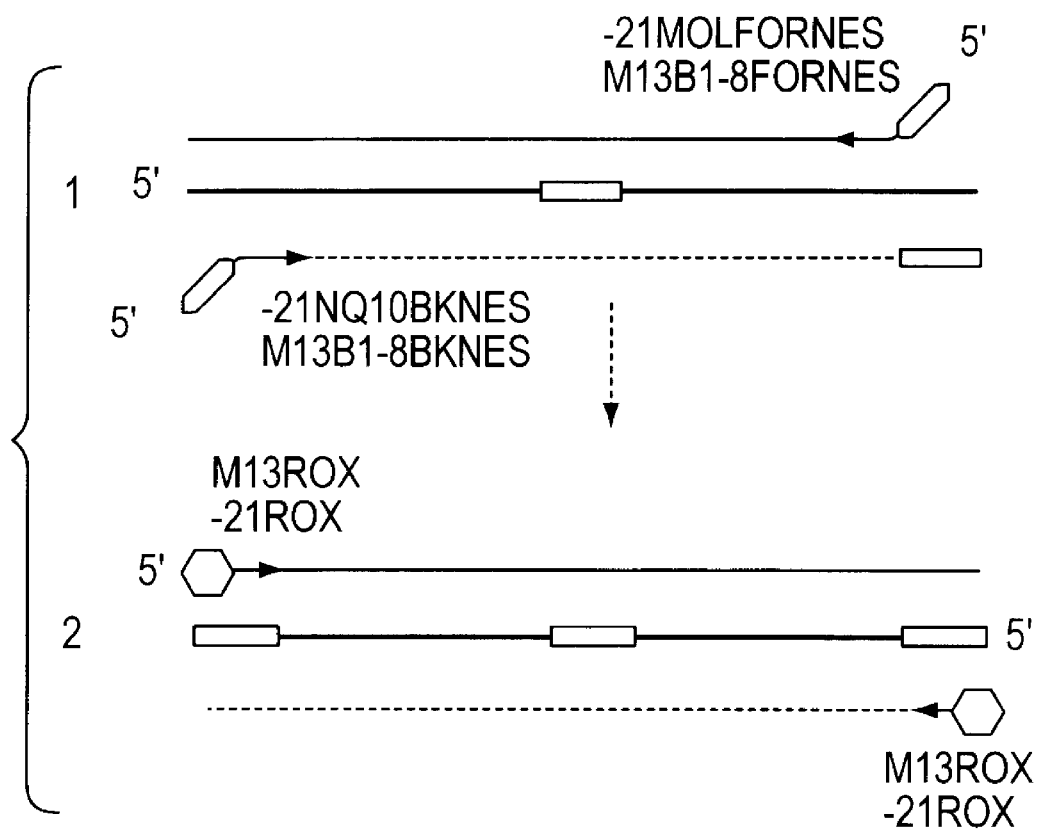
FIG. 7 illustrates schematically nested amplification of assembled Ig v-genes for fluorescent labelling.

FIG. 7 illustrates nested amplification of assembled Ig V-genes for fluorescent labelling. In this Figure, (1) shows second "nested" PCR with tagged primers to introduce primer sites for "universal" fluorescent primers and (2) shows third PCR with fluorescent primers. The same fluorescent primer can prime at both the 5' and 3' ends of the tagged sequences.

The cells were examined and photographed on a MRC 500 scanning laser confocal microscope (BioRad). Between $10^3$ and $10^4$ cells in 10 ul TE were spread on a glass slide and covered with a coverslip, sealed at the edges with nail varnish. In addition, cytofluorographic analysis was performed on a FACScan flow cytometer (Becton Dickinson). Fluorescence data were displayed as logarithmic overlay histograms using Consort 30 software (Becton Dickinson). Cell debris was gated out and $10^5$ cells were analysed per sample.

Cloning of assembled genes

DNA from the supernatant of cells after assembly and amplification was purified from 1.5% agarose gels in 0.5×

Tris-borate EDTA (TBE) buffer (pH 8.0) with ethidium bromide (0.5 ug/ml) incorporated into the gels. The assembled DNA bands of around 600 bp were eluted with Geneclean II (BIO 101 Inc.), with the addition of Geneclean 'TBE modifier'. The purified DNA was ligated into a 'T vector' derived from Bluescript KS+ (Stratagene) (24), and the vector transfected into E. coli CMK603 by electroporation. The cells were grown overnight on TYE plates (25) with 100 ug/ml ampicillin, 5-bromo-4-chloro-indolyl-B-D-galactoside (26) and isopropyl-B-D-1-thio-galactopyranoside (27). White colonies were replica plated in order to prepare colony lifts for hybridisation, or for use as templates for PCR screening.

For PCR screening of colonies (28), the reactions were set up in 20 ul volumes in individual wells of Hi-temp plates (Techne), containing 8 pmol of forward and back primers, 200 uM dNTPs, 2 ul 10× Taq buffer and 0.4 units Taq polymerase per well. For example to identify clones from the in-cell PCR of mixed hybridomas NQ10 and B1-8, each clone was screened with the primers NQ10BKNES and MOLFORNES, B1-8BKNES and B1-8FORNES, NQ10BKNES and B1-8FORNES, and B1-8BKNES and MOLFORNES. Each well was inoculated with bacteria from a single replica plated colony by means of a toothpick, and overlaid with 50 ul of mineral oil. The plates were subjected to 30 cycles of 95° C. for 30 secs, 65° C. for 1 min and 72° C. for 1 min on a Techne PHC-3 heat block designed for multi-well plates. The PCR products were run on 1.5% agarose gels (10 ul per lane).

For colony hybridisation, bacterial colony lifts were made using Hybond.-N nylon membranes (Millipore). The bacteria were lysed with sodium dodecyl sulphate and the DNA denatured and fixed to the membrane by microwaving (29), followed by UV cross-linking. Oligonucleotide probes for heavy (V186.2) and light (B1-8LPRB) chains of the B1-8 hybridoma, and heavy (NQ10PRB) and light (NQ10KPRB) chains of the NQ10/12.5 hybridoma, were labelled with gamma 32p-ATP using polynucleotide kinase (New England BioLabs) and hybridised to the nylon filters for 16 to 60 hours. The filters were washed with solutions containing tetramethylammonium chloride (21) and exposed on Kodak XAR 5 film.

In-cell PCR from mRNA (results)

In earlier work, cells infected with lentivirus had been fixed with paraformaldehyde and stored in ethanol (15). We fixed the hybridoma and leukaemia cells with formal saline, permeabilised them with NP40, and stored the cells frozen in PBS/0.1 M glycine. We found that with these cells, our method resulted in high yields of amplified DNA as detected in the cell supernatant (see below). The fixed and permeabilised cells remained intact during temperature cycling, and in PCRs from genomic DNA with primers specific for the VH and Vk regions of the hybridoma lines NQ2/12.4 and NQ10/12.5 (NQ10), amplified products of around 300 bp were routinely obtained in the cell supernatants. Permeabilisation was a necessary step, but formaldehyde concentrations ranging from 4% to 10% were equally effective for fixation. However, fixed and permeabilised cells which had undergone cDNA synthesis provided a much better template for PCR Supernatants from cDNA amplifications were run on a 1.5% agarose gel in TBE buffer. These are phi X174 HaeIII marker; PCR of B1-8 VH from fixed cells (formalin only); PCR of B1-8 VH from fixed and permeabilised cells (formalin and NP40); PCR assembly of B1-8 VH and V lambda from fixed and permeabilised cells; as the previous PCR assembly reaction except using nested primers in second PCR; as the previous PCR assembly reaction except with fixed cells; as the previous three PCR assembly reactions but with NQ10/ 12.5 hybridoma.

Consistently higher yields of amplified DNA were obtained when cells were added to the reaction in their storage buffer (PBS/0.1M glycine) rather than water. In NQ10 cells subjected to two-stage PCR assembly in which 10 uCi (25 pmol) $^{35}$S-dATP was added to label the first PCR, 70% of the radiolabelled product was found in the supernatant after the second PCR and 30% was retained within the cells.

The amplified DNA within the cells could be visualised directly by confocal microscopy (or conventional fluorescence microscopy) by incorporation of a fluorescent PCR primer in a third PCR step (30).

Figure 8A:
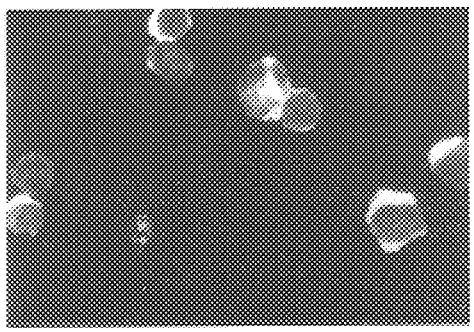
FIGS. 8A–F illustrate intracellular localisation of amplified cDNA in cells using fluorescence labelling.
Figure 8B:
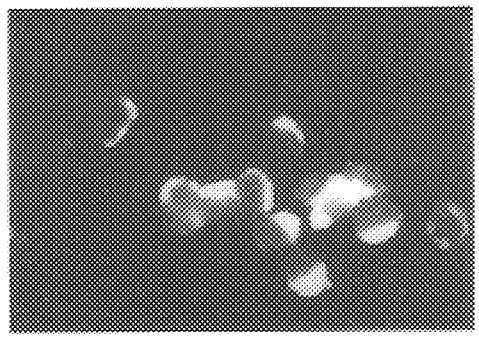
Figure 8C:
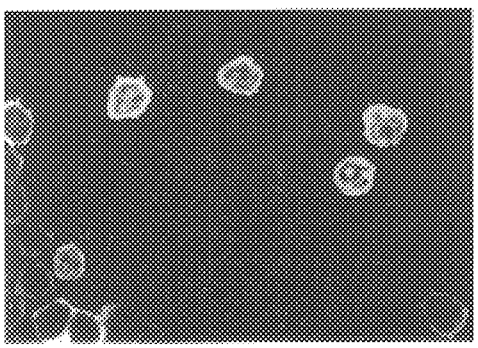
Figure 8D:
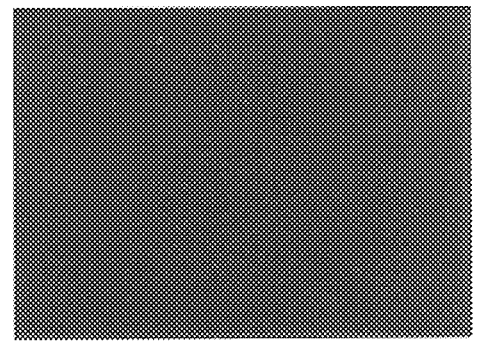
Figure 8E:
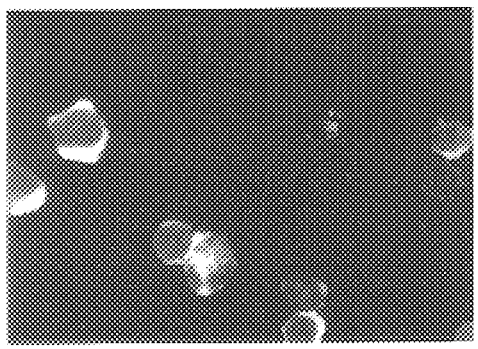
Figure 8F:
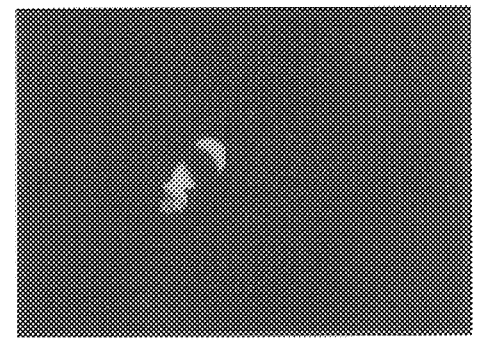

Confocal microscopy was used to detect the cDNA amplified with fluorescent PCR primers (see Table 1 for details of primers and controls). The results are shown in FIGS. 8A–F in which FIG. 8A shows PCR amplification of VH gene in NQ10/12.5 cells, FIG. 8B shows amplification of VH gene in B1-8 cells, FIG. 8C shows PCR assembly and nested amplification of VH and Vk genes in NQ10/12.5 cells, FIG. 8D shows PCR amplification of VH gene in NQ10/12.5 cells, and tagging using –21NQ10 primers in the second PCR, and M13ROX in the third PCR, FIG. 8E shows PCR assembly and nested amplification of VH and V lambda in B1-8 cells, and FIG. 8F shows PCR amplified bcr-abl in K562 cells.

Flow cytometry of K562 cells with amplified bcr-abl was also carried out, and the results are shown in FIGS. 9A for PCR amplification and labelling of cells with specific (–21) or non-specific (M13) ROX or FAM labelled primers, as in Table 1. In the FIG. 9A shows excitation detected in the red channel; –21ROX (solid line) and M13ROX (dotted line) and FIG. 9B shows excitation detected in the green channel; FAM labelled primers –21FAM (solid line) and M13FAM (dotted line).

The correct combinations of primers for NQ10/12.5 produced strong fluorescence in NQ10/12.5 (and not in B1-8 cells), and vice versa for B1-8 (Table 1, FIG. 9). The fluorescence was brighter for PCR assembled DNA than for PCR amplified VH DNA, perhaps due to the use of two fluorescent PCR primers or the greater retention of the longer DNA species within the cell (15). Although there were differences in fluorescence intensity among different cells, most of the cells amplified with the correct primers were fluorescent. The bcr-abl fusion gene in K562 cells subject to in-cell PCR could be detected by fluorescence microscopy FIG. 8A–F, and also by flow cytometry (FACS) FIG. 9A–B. The fluorescence was located in the cytoplasm, and FACS analysis confirmed that the majority of the cells were fluorescent. Amplification of the bcr-abl gene using the chosen primers confirmed the synthesis of cDNA in-cell prior to PCR, since the amplified portion (318 bp) contained three introns (21).

In-cell PCR assembly

B1-8 and NQ10 cells were fixed, permeabilised and mixed in equal ratios. The mixtures were then treated to cDNA synthesis and PCR amplification and assembly (FIG. 6), and the linked product isolated from the supernatant and cloned. The clones were then screened for the four different combinations of heavy and light chains (as described elsewhere). The results of three independent experiments are shown in Table 2 for 1:1 mixtures. In all cases the in-cell PCRs resulted in linkage of NQ10 VH with V Kappa, or B1-8 VH with V lambda, corresponding to the combinations of the hybridomas; no "crossovers" were seen in the 104 clones evaluated. By contrast, PCRs performed with soluble cDNA led in addition to cross-over combinations of NQ10 VH with V lambda and B1-8 VH with V Kappa.

These findings were confirmed for colonies from the first experiment in Table 2, by hybridising blots of replica plated bacterial colonies with $^{32}$-P labelled oligonucleotide probes for internal sequences of the four V-genes (V186.2, B1-8LPRB, NQ10PRB and NQ10KPRB). Again in-cell PCRs gave rise to clones with the combinations of the hybridomas, while clones from the soluble cDNA resulted in additional cross-over combinations (Table 2).

A more stringent test of VH and VL linkage was performed by PCR of cell and soluble cDNA templates from a mix containing 10% B1-8 cells and 90% NQ10/12.5 cells (Table 3). In this case, 450 clones of each PCR assembly were initially probed with $^{32}$p kinase labelled V186.2 oligonucleotide probe to identify those clones expressing the B1-8 VH chain. The positive clones were then screened on agarose gels to detect either V Kappa and V lambda genes using PCR with the primers MOVKLINK3 and MOLFORNES, and B1-8VLLINK3 and B1-8FORNES respectively. From the in-cell PCR, all the B1-8 VH clones (27) were all linked to the V lambda chain. From the assembly from soluble cDNAs, 3 of the 34 B1-8 VH positive clones were linked to the V lambda chain, and 31 to the V Kappa chain.

EXAMPLE 4

Linking of Human Immunoglobulin Heavy and Light Chain Variable Domain Genes from a Mixed Lymphocyte Population We describe a further example linking the human immunoglobulin (Ig) variable region genes (VH and VL) within single cells in a lymphocyte population, such that the assembled products can be cloned into a vector and expressed as soluble antibody fragments or displayed on the surface of phage. In essence, it comprises synthesis of cDNA using forward primers annealing to the Ck gene and the JH segment, followed by assembly with linker primers, VH back primers based on the VH3 leader sequence, and a forward Ck primer nested with respect to the primer used for cDNA. The assembled product within the cells is then amplified with nested primers annealing to the 5' end of the VH gene and the 3' end of the Jk segment.

Cells

Heparinised human blood was layered onto Lymphoprep lynphocyte separation medium (Nycomed) in a 50 ml centrifuge tube, using equal volumes of undiluted blood and Lymphoprep. Tubes were centrifuged at 4,000× g for 20 minutes, after which mononuclear cells (which include lymphocytes) were visible as a band separating the blood plasma (upper layer) and the Lymphoprep (lower layer).

The cells were removed and washed 3 times in phosphate buffered saline (PBS, pH 7.2), and incubated in 10% formaldehyde in 0.15M NaCl solution on ice for 1 hour. They were again washed in PBS 3 times, followed by incubation on ice in 0.5% Nonidet P40 (BDH) in water. After a further 3 washes in PBS the cells were suspended in PBS containing 0.1M glycine and counted. They were stored frozen at –70° C.

Oligonucleotide primers

The following primers were used in cDNA first strand synthesis and the PCRs.

| | | |
|---|---|---|
| VH3LDR1 | (SEQ ID NO: 36) | 5' GCT (A/C)TT TTA A(G/A)A CGT GTC CAG TGT 3' |
| VH3LDR2, | (SEQ ID NO: 37) | 5' GGT ATT TTA CAA GGT GTC CAG TGT 3' |
| VH3LDR3, | (SEQ ID NO: 38) | 5' GCT ATA TTA (A/G)(A/G)A GGT GCC CAG TGT 3' |

-continued

| | | |
|---|---|---|
| VH3a, | (SEQ ID NO: 39) | 5' GAG CTG CAG CTG CTG GAG TCT GG 3' |
| VH3aSfi | (SEQ ID NO: 40) | 5' GTC CTC GCA ACT GCG GCC CAG CCG GCC ATG GCC GAG CTG CAG CTG CTG GAG TCT GG 3' |
| JH4-5A | (SEQ ID NO; 41) | 5' GAA CCC TGG TCA CCG TCT CCT CAG GTG G 3' |
| JH6AFOR | (SEQ ID NO: 42) | 5' GGA CCA CGG TCA CCG TCT CCT CAG GTG C 3' |
| Ck5'FOR | (SEQ ID NO: 43) | 5' GGA AGA TGA AGA CAG ATG TGT CAG 3' |
| CkEXTF | (SEQ ID NO: 44) | 5' CAG ATT TCA ACT GCT CAT CAG ATG G 3' |
| Jk1FOR | (SEQ ID NO: 45) | 5' ACG TTT GAT TTC CAC CTT GGT CCC 3' |
| Jk2FOR | (SEQ ID NO: 46) | 5' ACG TTT GAT CTC CAG CTT GGT CCC 3' |
| Jk3FOR | (SEQ ID NO: 47) | 5' ACG TTT GAT ATC CAC TTT GGT CCC 3' |
| Jk4FOR | (SEQ ID NO: 48) | 5' ACG TTT GAT CTC CAC CTT GGT CCC 3' |
| Jk5FOR | (SEQ ID NO: 49) | 5' ACG TTT AAT CTC CAG TCG TGT CCC 3' |
| Jk1FORNot | (SEQ ID NO: 50) | 5' GAG TCA TTC TCG ACT TGC GGC CGC ACG TTT GAT TTC CAC CTT GGT CCC 3' |
| Jk2FORNot | (SEQ ID NO: 51) | 5' GAG TCA TTC TCG ACT TGC GGC CGC ACG TTT GAT CTC CAG CTT GGT CCC 3' |
| Jk3FORNot | (SEQ ID NO: 52) | 5' GAG TCA TTC TCG ACT TGC GGC CGC ACG TTT GAT ATC CAC TTT GGT CCC 3' |
| Jk4FORNot | (SEQ ID NO: 53) | 5' GAG TCA TTC TGC GGC CGC ACG TTT GAT CTC CAC CTT GGT CCC 3' |
| Jk5FORNot | (SEQ ID NO: 54) | 5' GAG TCA TTC TCG ACT TGC GGC CGC ACG TTT AAT CTC CAG TCG TGT CCC 3' |
| JHLINK 1,2 | (SEQ ID NO: 55) | 5' CCA GAG CCA CCT CCG CCT GAA CCG CCT CCA CCT GAG ACG GTG ACC AGG GT(C/T) CC 3' |
| JH3LINK | (SEQ ID NO: 56) | 5' CCA GAG CCA CCT CCG CCT GAA CCG CCT CCA CCT GAG ACG GTG ACC ATT GTC CC 3' |
| JH6LINK | (SEQ ID NO: 57) | 5' CCA GAG CCA CCT CCG CCT GAA CCG CCT CCA CCT GAG GAG ACG GTG ACC GTG GTC CC3' |
| VkLINK | (SEQ ID NO: 58) | 5' CAG GCG GAG GTG GCT CTG GAG GTG GCG GAT CGG AAA TTG TGT TGA CGC AGT CTC C 3' |
| VkLINK1 | (SEQ ID NO: 59) | 5' CAG GCG GAG GTG GCT CTG GAG GTG GCG GAT CGG ACA TCC AGA TGA CCC AGT CTC C 3' | cDNA first strand synthesis

Aliquots of $5\times10^5$ fixed and permeabilised cells were thawed and washed once in water, and resuspended in 20 ul water. The following "first strand" mix was prepared: 5 ul 10×1st strand buffer (1.4M KCl, 0.5M Tris-HCl pH 8.1 at 42° C., 80 mM $MgCl_2$), 5 ul 0.1M dithiothreitol, 5 ul 5 mM dNTPs, 25 pmol each primers JH4-5A, JH6AFOR and CkEXTF, 80 units of RNase inhibitor (RNasin, Promega) and water to 28ul. The cells were heated to 65° C. for 3 minutes and cooled on ice. They were then added to the 1st strand mix together with 40 units of Super RT AMV reverse transcriptase, and the whole mixture incubated at 42° C. for 1 hour. The cells were then spun down, washed once in PBS/0.1M glycine and resuspended in the same buffer for PCR.

Reactions were set up in 50ul volumes in 0.5 ml Sarstedt tubes, using $10^5$ cDNA template cells in 10 μl together with a mix containing 25 pmol VH back primer mix (VH3LDR1+ VH3LDR2 +VH3LDR3), 25 pmol Ck5'FOR, 10 pmol linker primer mix (JHLINK 1,2+JH3LINK+JH6LINK+VkLINK+ VkLINK1), 200 uM dNTPs, 5 ul 10×Taq polymerase buffer (Promega) and 2.5 unit Taq polymerase. The tubes were subjected to 30 cycles of PCR with denaturation at 95° C. for 30 seconds, annealing for 58° or 65° C. for 30 seconds, and extension at 72° C. for 30 seconds, in a thermal cycling oven (BioTherm Corp. "BioOven") without an oil overlay. This was referred to as the "1st PCR".

The cells were spun down and washed twice in PBS/0.1M glycine, and suspended in 10 μl of this buffer for a 2nd PCR together with the following mix:

200 uM dNTPs, 5ul 10× Taq buffer, 2.5 units Taq polymerase, and either of primer combinations (a) 25 pmol VH3A and 25 pmol of a mix of Jk1FOR+Jk2FOR+ Jk3FOR+Jk4FOR+Jk5FOR, or (b) 25 pmol VH3ASfi and 25 pmol of a mix of Jk1FORNot+JK2FORNot+ Jk3FORNot+Jk4FORNot+Jk5FORNot. Water was added to bring the cells and reagents to 50 ul, and PCR cycling was carried out as for the first stage. When primer combination (a) was used in the 2nd PCR, the cells were recovered and washed, and treated to a 3rd PCR with primer combination (b) to append restriction sites for cloning.

The PCR products were analysed by running on 1.5% agarose gels in 0.5×Tris-borate-EDTA buffer containing 0.5 ug/ml ethidium bromide and viewing under ultra-violet light.

RESULTS

Assembly using a two-PCR protocol with primers incorporating restriction sites in the 2nd PCR (primer combination (b)), or a three-PCR protocol with primer combination (a) in the 2nd PCR and (b) in the 3rd, resulted in a band of DNA of the size expected for an assembled VH3 - Vk antibody fragment (about 700 bp). Since this fragment would include VH3 Sfi and Vk Not restriction sites, it could be digested with the appropriate enzymes and cloned into the vector pHEN (references 38, 41). This would allow expression as cloned fusion products displayed on the surface of phage if introduced into a suppressor strain of E. coli such as TG1, or as soluble single chain Fv fragments with a C terminal peptide tag following infection of a non-suppressor strain such as HB2151 (38). Although this example made use of primers designed for k light chains and the VH3 family the process is equally applicable to other human heavy and light chain families, and primers could be designed accordingly (38).

Discussion of Examples

Earlier work had shown that the DNA of lentivirus infected cells could be PCR amplified in infected cells and detected by autoradiography (15), and more recently HIV provirus has been detected by PCR amplification and peroxidase staining in cells attached to glass slides (31). In-cell PCR allows the genes of individual cells to be amplified, but without the need to place each cell in a separate tube (32). It partitions the amplification of a cell population, allowing many independent reactions in the same tube. We have extended the use of in-cell PCR by reverse transcription of mRNA to cDNA within single cells of a suspension (Example 3). The cDNA is retained within the cell and allows PCR amplification. Furthermore the amplified DNA could be fluorescence labelled within the cell using fluorescent PCR primers, and should allow the analysis of large and diverse populations of cells by fluorescence. Here we used three PCR amplifications in order to tag the amplified DNA, and then fluorescence lable and tagged DNA with "universal" fluorescent PCR primers. However, it should also be possible to fluorescence label the cDNAs within the cell with a single PCR amplification using a set of fluorescent PCR primers specifically made for the gene of interest.

In-cell PCR from CDNA appears to be efficient, as most of the cells of the hybridomas and K562 myeloid leukaemia could be fluorescence labelled, as determined by confocal microscopy FIG. 8A–F or FACS FIG. 9A–B. A potential advantage of fluorescence labelling over use of radiolabelled probes is that rare positive cells could be isolated by FACS, and their genes cloned directly or after further rounds of PCR.

We were able to assemble the PCR amplified DNA from two mRNAs of the same cell and to amplify the assembled DNA using nested primers, allowing the combinations of linked genes to be identified by fluorescence (Table 1), and to be cloned. For mixtures of two hybridomas, the original combinations of the hybridoma V-genes were retained even with one hybridoma in ten told excess. The extent of linkage between two markers of one cell is likely to depend inter alia on whether both mRNAs are amplified efficiently and to high copy number, and on whether there is competition from amplified DNA leaking from other cells to take part in the assembly process. After the first PCR, we therefore washed the cells to remove DNA from their surface or outer layers before using the second "nested" PCR to amplify those V-genes assembled within individual cells. The strong linkage we see between the V-genes within the same cell may allow even rare combinations of genes to be rescued from a large population of cells.

In-cell PCR and assembly has many potential uses for gene linkage analysis, but a major application is likely to be the cloning of gene combinations that are polymorphic within a population of cells, such as the rearranged genes for Ig or TCR V regions. The linked genes could be cloned for probing, sequencing or expression. Thus in example 4, the way we have assembled the V-genes allows the cloning of the linked product directly into expression vectors. Such a process would provide alternatives to B and T-cell hybridomas, allowing the original V-gene combinations to be cloned directly into vectors for expression in mammalian cells (5) or bacteria (33,34,35,36,37) or displayed on the surface of filamentous bacteriophage (9). By antigen panning of filamentous bacteriophage displaying antibody fragments, even very rare clones could be isolated (9,38), and this should facilitate analysis of the V-gene combinations, smatic mutation, affinities and specificities of natural, immune and auto-immune B-cells. Table 1. In cell PCR with fluorescence labelled primers

TABLE 1

In cell PCR with fluorescence labelled primers

| cells | Primers PCR1 | Primers PCR2 | Primers PCR3 | Fluorescent Cells |
|---|---|---|---|---|
| NQ10 (VH gene) | NQ10BK MOJH3FOR | −21NQ10BKNES MOJH3FOR | −21 ROX M13 ROX | + − |
| NQ10 (VH gene) | B1-8BK B1-8VHLINK3 | M13B1-8BKNES V186.2 | −21 ROX M13 ROX | − − |
| B1-8 (VH gene) | NQ10BK MOJH3FOR | −21NQ10BKNES MOJH3FOR | −21 ROX M13 ROX | − − |
| B1-8 (VH gene) | B1-8BK B1-8VHLINK3 | M13B1-8BKNES V186.2 | −21 ROX M13 ROX | − + |
| NQ10 (VH/VK genes) | NQ10BK MOVHLINK3 MOVKLINK3 MOLFOR | −21NQ10BKNES −21MOLFORNES | −21 ROX M13 ROX | + − |
| B1-8 (VH/VL genes) | B1-8VHBK B1-8VHLINK3 B1-8VHLINK3 B1-8LFOR | M13B1-8BKNES M13B1-8FORNES | −21 ROX M13 ROX | − + |
| K562 (bcr-ab1) | ABL2C BCR1A | −2BCRB −21ABL2D | −21 ROX M13 ROX | + − |
| K562 (bcr-ab1) | ABL2C BCR1A | −21BCRB −21ABL2D | −21 FAM M13 FAM | + − |

TABLE 2

Screening of linked VH and VL gene combinations from 1:1 mixtures of B1-8 and NQ10/12.5 hybricloma cells.

| PCR template | VH/VL combination | Expt. 1 | Expt. 1 (probe) | Expt. 2 | Expt. 3 |
|---|---|---|---|---|---|
| Fixed cells | NQ10VH NQ10 Vκ | 20/47 | 19/32 | 11/36 | 11/21 |
| " | B1-8 VH B1-8 Vλ | 27/47 | 13/32 | 25/36 | 10/21 |
| " | NQ10 VH B1-8 Vλ | 0/47 | 0/32 | 0/36 | 0/21 |
| " | B1-8 VH NQ10 Vκ | 0/47 | 0/32 | 0/36 | 0/21 |
| Random combinatorial | NQ10 VH NQ10 Vκ | 2/49 | 11/103 | 0/44 | 10/24 |
| Random combinatorial | B1-8 VH B1-8 Vλ | 27/49 | 56/103 | 40/44 | 4/24 |
| Random combinatorial | Nq10 VH B1-8 Vλ | 10/49 | 14/103 | 2/44 | 4/24 |
| Random combinatorial | B1-8 VH NQ10 Vκ | 10/49 | 22/103 | 2/44 | 6/24 |

PCR templates were derived from a 1:1 mix of NQ10/12.5 and B1-8 cells which were divided into two portions. One portion of the cells were fixed before cDNA synthesis and PCR assembly and nested amplification (Fixed cells), and the other was boiled in water for cDNA synthesis and PCR assembly and nested amplification from soluble mRNA (Random combinatorial). Colonies were screened by PCR for Expts 1, 2 and 3, but extra Expt. 1 colonies were also probed.

TABLE 3

Screening of linked VH and VL gene combinations from 1:9 mixtures of B1-8:NQ10/12.5 hybridoma cells.

| PCR template | Clones with B1-8 VH (probed) | Clones with B1-8 VH and B1.8 Vλ | Clones with B1-8 VH and NQ10/12.5 Vκ |
|---|---|---|---|
| Fixed cells | 27/450 | 27/450 | 0/450 |
| Random combinatorial | 34/450 | 3/450 | 31/450 |

For preparation of PCR assembly templates a 1:9 mix of B 1-8 : NQ10/12.5 cells was divided into two portions. One portion was fixed for cDNA synthesis and PCR (Fixed cells), and the other was boiled in water for cDNA synthesis and PCR from soluble mRNA (Random combinatorial). Clones were probed with 32p labelled V186.2 probe, and those clones identified with B 1.8 VH genes were PCR screened for either Vλ or Vκ genes.

REFERENCES

1. Wick, M R, Loy, T, Mills, S E, Legier, J F, and Manivel, J L (1990). Hum.Path., 21, 758–766.
2. Waldmann, T A, (1991). Science, 252, 1657–1662.
3. Hammarstrom, S, Shively, J E, Paxton, R J, Beatty, B G, Larsson, A, Ghosh, R, et al. (1989). Cancer Res., 49, 4852–4858.
4. Barber, K E, Grosier, P S, Purdie, K J, Buchanan, J M, Cattermole, J A, Watson, J D, and Gillis, S (1989). Growth Factors, 1, 101–114.
5. Orlandi, R, Gussow, D H, Jones, P T, and Winter, G (1989). Proc. Natl. Acad. Sci. USA, 86, 3833–3837.
6. Sastry, L, Alting-Mees, M, Huse, D W, Short, J M, Hay, B N, Jainda, K D, Benkovic, S J, and Lerner, R A (1989). Proc. Natl. Acad. Sci. USA, 86, 5728–5732.
7. Ward, E S, Gussow, D, Griffiths, A D, Jones, P T, and Winter, G (1991). Nature, 349, 293–299.
8. Huse, D W, Sastry, L, Iverson, S A, Kang, A S, Alting-Mees, M, Burton, D R, Benkovic, S J, and Lerner, R A (1989). Science, 246, 1275–1281.
9. McCafferty, J, Griffiths, A D, Winter, G, and Chiswell, D J (1990). Nature, 346, 552–554.
10. Clackson, T, Hoogenboom, H R, Griffiths, A D, and Winter, G (1991). Nature, 352, 624–628.
11. Winter, G, and Milstein, C, (1991). Nature, 349, 293–299.
12. Gherardi, E, and Milstein, C, (1992). Nature, 357, 201–202.
13. Kang, A S, Barbas, C F, Janda, K D, Benkovic, S J, and Lerner, R A (1991). Proc. Natl. Acad. Sci. USA, 88, 4363–4366.
14. Zebedee, S L, Barbas, C F III, Hom, Y L, Caothien, R H, Graff, Rr DeGraw, J, Pyati, J, LaPolla, R, Burton, D R, Lerner, R A and Thornton, G B (1992). Proc. Natl. Acad. Sci. USA, 89, 3175–3179.
15. Haase, A T, Retzel, E F, and Staskus, K A (1990). Proc. Natl. Acad. Sci. USA, 87, 4971–4975.
16. Cumano, A and Rajewsky, K (1985). Eur. J Immunol., 15, 512–520. Nature, 312, 272–276.
17. Griffiths, C M, Berek, C, Kaartinen, M, and Milstein, C (1987). Nature, 312, 272–276.
18. Andersson, L C, Nilsson, K, and Gahmberg, C G (1979). Int. J. Cancer, 23, 143–147.
19. Heisterkamp, N, Stem, K, Groffen, J, de Klein, A, and Grosveld, G (1985). Nature, 315, 758–761.
20. Ausubel, F M, Brent, R, Kingston, R E, Moore, D D, Seidman, D D, Smith, J A, and Struhl, K (1990). Current Protocols in Molecular Biology, Greene Publishing Associates and Wiley-Interscience, New York.
21. Thompson, J D, Brodsky, I, and Yunis, J J (1992). Blood, 79, 1629–1635.
22. Davis, G T. Bedzyk, W D, Voss, E W. and Jacobs, T W (1991). Biotechnology, 9, 165–169.
23. Albert, J and Fenyo, E M (1990). J. Clin. Microbiol., 28, 1560–1564.
24. Marchuk. D, Drumm, M, Saulino, A, and Collins, F S (1991). Nucl. Acids Res., 19, 1154.
25. Miller, J H (1972) Experiments in Molecular Genetics, Cold Spring Harbor Laboratory Press, Cold Spring Harbor, New York.
26. Horowitz, J P, Chua, J, Curby, R J, Tomson, A J, Da Rooge, M F Fisher, B E, Mauricio, J, and Klundt, I (1964). J. Med. Chem., 7, 574–575.
27. Cho, S, Scharpf, S, Franko, M, and Vermeulen, C W (1985). Biochem. Biophys. Res. Comm., 128, 1268–1273.
28. Gussow, D and Clackson, T (1989). Nucl. Acids Res., 17, 4000.
29. Bulwela, L, Forster, A, Boehm, T, and Rabbitts, T H (1989). Nucl. Acids Res., 17, 452.
30. Chebab, F F, and Kan, Y W (1989). Proc. Natl. Acad. Sci. USA, 86, 9178–9182.
31. Bagasra, 0, Hauptman, S P, Lischner, H W, Sachs, M, and Pomerantz, R J (1992). New Engl. J. Med., 326, 1385–1391.
32. Li, H H, Gyllensten, U B, Cui, X F, Saiki, R K, Erlich, H A and Arnheim, N (1988). Nature, 335, 414–417.
33. Skerra, A, Pfitzinger, I, and Pluckthun, A (1991). Biotechnology, 9, 273–278.
34. Better, M, Chang, C P, Robinson, R R, and Horwitz, A H (1988). Science, 240, 1041–1043.
35. Novotny, J, Ganju, R K, Smiley, S T, Hussey, R E, Luther, M A, Recny, M A, Siliciano, R F, and Reinherz, E L (1991). Proc. Natl. Acad. Sci., USA, 88, 8646–8650.
36. Soo Hoo, W F, Lacy, M J, Denzin, L K, Voss, E W, Hardman, K D, and Kranz, D M (1992). Proc. Natl. Acad. Sci. USA, 89, 4759–4763.
37. Ward, E S (1992). J. Mol. Biol., 224, 581–579.
38. Marks, J D, Hoogenboom, H R, Bonnert, T P, McCafferty, J, Griffiths, A D and Winter, G (1991). J. Mol. Biol., 222, 581–579.
39. Li et al. (1988). Nature 345, 414–417.
40. Engelke et al. (1990). Anal. Biochem. 191, 396–400.
41. Hoogenboom, H R, Griffiths, A D, Johnson, K S, Chiswell, D J, Hudson, P and Winter, G (1991). Nucl. Acids Res., 19, 143–151.

We claim:

1. A method of treating a population of cells to link together copies of two or more non-contiguous DNA sequences from at least some of the cells, comprising treating the cells to stabilise them with respect to temperature and to permeabilise them with respect to reagents; adding primers for performing the polymerase chain reaction (PCR) such that the primers diffuse into the interior of the cells; subjecting the cells to suitable treatment so the DNA sequences of a particular cell are copied within that cell by PCR; and linking together within the cell the copies of the DNA sequences.

2. A method according to claim 1, wherein the DNA sequence copies are linked by PCR.

3. A method according to claim 1, wherein the DNA sequence subjected to PCR is derived from cellular mRNA.

4. A method according to claim 3, wherein the DNA sequence is cDNA derived by reverse transcription of 1 mRNA.

5. A method according to claim 1, further comprising a washing step following said linking of DNA.

6. A method according to claim 1, further comprising one or more rounds of PCR.

7. A method according to claim 6, wherein further rounds of PCR are performed using "nested" primers.

8. A method according to claim 1, wherein the DNA sequences comprise sequences encoding immunoglobulin VH and VL domains.

9. A method according to claim 1, wherein the resulting DNA is cloned by insertion into a suitable vector.

10. A method according to claim 9, whereby the clones are sequenced or annealed to nucleic acid probes.

* * * * *

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:1:

CAGGTGCAGC TGAAGGAGTC AGG 23

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:2:

TGCAGCTGGT GGAGTCTGGG GG 22

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:3:

CTTACGTTTC AGCTCCAGCT TGG 23

( 2 ) INFORMATION FOR SEQ ID NO:4:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:4:

CCACTGCCGC CACCACCGCT ACCACCACCA CCTGCAGAGA CAGTGACCAG        50

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:5:

CAATTTGGCT AGCTGCAGAG ACAGTGACCA GAGTCCCTTG GCCCCA        46

( 2 ) INFORMATION FOR SEQ ID NO:6:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:6:

GCGGTGGTGG CGGCAGTGGC GGCGGCGGCT CTCAAATTGT TCTCACCCAG TCTCCAGC        58

( 2 ) INFORMATION FOR SEQ ID NO:7:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:7:

CAGTGTCTCT GCGCTAGCCC AAATTGTTCT CACCCAGTCT CCAG        44

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:8:

CCCAGCACCG AACGTGAGTG G        21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:9:

CGCCCTCACA GAGCCTGTCC A        21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:10:

AGCCTGGAGG GTCCCGGAAA C        21

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:11:

CTTACGTTTC AGCTCCAGCT TGG        23

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:12:

TAGGACTCAC CTGCAGAGAC AGTG        24

( 2 ) INFORMATION FOR SEQ ID NO:13:

( i ) SEQUENCE CHARACTERISTICS:
        ( A ) LENGTH: 23 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO:13:

GCCTAGGACA GTCAGTTTGG TTC 23

(2) INFORMATION FOR SEQ ID NO:14:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO:14:

CCACTGCCGC CACCACCGCT ACCACCACTG AGGAGACTGT GAGAGTGGTG C 51

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO:15:

CAGGTGCAGC TGAAGGAGTC AGG 23

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO:16:

TGCAGCTGGT GGAGTCTGGG GG 22

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:17:

CAGGTCCAAC TGCAGCAGCC TG 22

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:18:

AGTTACACGT TCCTGATCTC 20

(2) INFORMATION FOR SEQ ID NO:19:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:19:

TTATCTCCAC TGGCCACAAA 20

(2) INFORMATION FOR SEQ ID NO:20:

(i) SEQUENCE CHARACTERISTICS:
(A) LENGTH: 58 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:20:

GCGGTGGTGG CGGCAGTGGC GGCGGCGGCT CTCAGGCTGT TGTGACTCAG GAATCTGC 58

(2) INFORMATION FOR SEQ ID NO:21:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO ( i i i ) ANTI-SENSE: NO ( x i ) SEQUENCE DESCRIPTION: SEQ ID NO:21:

GAGCTTGTGA AGCCTGGGGC TT 22

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:22:

CCCAGCACCG AACGTGAGTG G 21

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:23:

CCACCGAACA CCCAATGGTT GCT 23

( 2 ) INFORMATION FOR SEQ ID NO:24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:24:

AGACAAACCC TCCAG 15

( 2 ) INFORMATION FOR SEQ ID NO:25:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:25:

CAGGAAACAG CTATGACCGA GCTTGTGAAG CCTGGGGCT                                39

( 2 ) INFORMATION FOR SEQ ID NO:26:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:26:

CAGGAAACAG CTATGACCCC ACCGAACACC CAATGGTTGC T                             41

( 2 ) INFORMATION FOR SEQ ID NO:27:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:27:

TGTAAAACGA CGGCCAGTCC CAGCACCGAA CGTGAGTGG                                39

( 2 ) INFORMATION FOR SEQ ID NO:28:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:28:

TGTAAAACGA CGGCCAGTAC GCTGGAGGGT CCCGGAAAC                                39

( 2 ) INFORMATION FOR SEQ ID NO:29:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:29:

TGTAAAACGA CGGCCAGTTC TGACTATGAG CGTGCAGA                                 38

( 2 ) INFORMATION FOR SEQ ID NO:30:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:30:

TGTAAAACGA CGGCCAGTAG TGCAACGAAA AGGTTGGG                38

( 2 ) INFORMATION FOR SEQ ID NO:31:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:31:

TGTAAAACGA CGGCCCAG                18

( 2 ) INFORMATION FOR SEQ ID NO:32:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:32:

CAGGAAACAG CTATGAC                17

( 2 ) INFORMATION FOR SEQ ID NO:33:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:33:

CTGTACCATA GAGCACAG                18

( 2 ) INFORMATION FOR SEQ ID NO:34:

( i ) SEQUENCE CHARACTERISTICS:
    ( A ) LENGTH: 20 base pairs
    ( B ) TYPE: nucleic acid (C) STRANDEDNESS: single
                (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:34:

GAGTTTCCGG GACCCTCCAG 20

(2) INFORMATION FOR SEQ ID NO:35:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:35:

TTGGAACCAG TTCATGTAC 19

(2) INFORMATION FOR SEQ ID NO:36:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:36:

GCTMTTTTAA RACGTGTCCA GTGT 24

(2) INFORMATION FOR SEQ ID NO:37:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:37:

GGTATTTTAC AAGGTGTCCA GTGT 24

(2) INFORMATION FOR SEQ ID NO:38:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (i i) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:38:

GCTATATTAR RAGGTGCCCA GTGT 24

( 2 ) INFORMATION FOR SEQ ID NO:39:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:39:

GAGCTGCAGC TGCTGGAGTC TGG 23

( 2 ) INFORMATION FOR SEQ ID NO:40:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:40:

GTCCTCGCAA CTGCGGCCCA GCCGGCCATG GCCGAGCTGC AGCTGCTGGA GTCTGG 56

( 2 ) INFORMATION FOR SEQ ID NO:41:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:41:

GAACCCTGGT CACCGTCTCC TCAGGTGG 28

( 2 ) INFORMATION FOR SEQ ID NO:42:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:42:

GGACCACGGT CACCGTCTCC TCAGGTGC                              28

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:43:

GGAAGATGAA GACAGATGGT GCAG                                   24

( 2 ) INFORMATION FOR SEQ ID NO:44:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:44:

CAGATTTCAA CTGCTCATCA GATGG                                  25

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:45:

ACGTTTGATT TCCACCTTGG TCCC                                   24

( 2 ) INFORMATION FOR SEQ ID NO:46:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:46:

ACGTTTGATC TCCAGCTTGG TCCC                                   24

( 2 ) INFORMATION FOR SEQ ID NO:47:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:47:

ACGTTTGATA TCCACTTTGG TCCC    24

( 2 ) INFORMATION FOR SEQ ID NO:48:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:48:

ACGTTTGATC TCCACCTTGG TCCC    24

( 2 ) INFORMATION FOR SEQ ID NO:49:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:49:

ACGTTTAATC TCCAGTCGTG TCCC    24

( 2 ) INFORMATION FOR SEQ ID NO:50:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:50:

GAGTCATTCT CGACTTGCGG CCGCACGTTT GATTCCACC TTGGTCCC    48

( 2 ) INFORMATION FOR SEQ ID NO:51:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:51:

GAGTCATTCT CGACTTGCGG CCGCACGTTT GATCTCCAGC TTGGTCCC    48

( 2 ) INFORMATION FOR SEQ ID NO:52:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:52:

GAGTCATTCT CGACTTGCGG CCGCACGTTT GATATCCACT TTGGTCCC    48

( 2 ) INFORMATION FOR SEQ ID NO:53:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:53:

GAGTCATTCT CGACTTGCGG CCGCACGTTT GATCTCCACC TTGGTCCC    48

( 2 ) INFORMATION FOR SEQ ID NO:54:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO:54:

GAGTCATTCT CGACTTGCGG CCGCACGTTT AATCTCCAGT CGTGTCCC    48

( 2 ) INFORMATION FOR SEQ ID NO:55:

( i ) SEQUENCE CHARACTERISTICS:
        ( A ) LENGTH: 56 base pairs
        ( B ) TYPE: nucleic acid
        ( C ) STRANDEDNESS: single (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:55:

CCAGAGCCAC CTCCGCCTGA ACCGCCTCCA CCTGAGGAGA CGGTGACCAG GGTYCC 56

(2) INFORMATION FOR SEQ ID NO:56:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:56:

CCAGAGCCAC CTCCGCCTGA ACCGCCTCCA CCTGAAGAGA CGGTGACCAT TGTCCC 56

(2) INFORMATION FOR SEQ ID NO:57:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:57:

CCAGAGCCAC CTCCGCCTGA ACCGCCTCCA CCTGAGGAGA CGGTGACCGT GGTCCC 56

(2) INFORMATION FOR SEQ ID NO:58:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i i i) ANTI-SENSE: NO (x i) SEQUENCE DESCRIPTION: SEQ ID NO:58:

CAGGCGGAGG TGGCTCTGGA GGTGGCGGAT CGGAAATTGT GTTGACGCAG TCTCC 55

(2) INFORMATION FOR SEQ ID NO:59:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (i i) MOLECULE TYPE: DNA (genomic)

(iii) HYPOTHETICAL: NO (iii) ANTI-SENSE: NO (xi) SEQUENCE DESCRIPTION: SEQ ID NO:59:

CAGGCGGAGG TGGCTCTGGA GGTGGCGGAT CGGACATCCA GATGACCCAG TCTCC 55

(2) INFORMATION FOR SEQ ID NO:60:

(i) SEQUENCE CHARACTERISTICS:
      (A) LENGTH: 708 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iii) ANTI-SENSE: NO (ix) FEATURE:
      (A) NAME/KEY: CDS
      (B) LOCATION: 1..705

(xi) SEQUENCE DESCRIPTION: SEQ ID NO:60:

```
CAG GTG CAG CTG AAG GAG TCA GGA CCT GGC CTG GTG GCG CCC TCA CAG        48
Gln Val Gln Leu Lys Glu Ser Gly Pro Gly Leu Val Ala Pro Ser Gln
 1               5                  10                  15

AGC CTG TCC ATC ACT TGC ACT GTC TCT GGG TTT TCA TTA ACC AGC TAT        96
Ser Leu Ser Ile Thr Cys Thr Val Ser Gly Phe Ser Leu Thr Ser Tyr
             20                  25                  30

GGT GTA CAC TGG GTT CGC CAG CCT CCA GGA AAG GGT CTG GAG TGG CTG       144
Gly Val His Trp Val Arg Gln Pro Pro Gly Lys Gly Leu Glu Trp Leu
         35                  40                  45

GGA GTA ATA TGG GCT GGT GGA AGC ACA AAT TAT AAT TCG GCT CTC ATG       192
Gly Val Ile Trp Ala Gly Gly Ser Thr Asn Tyr Asn Ser Ala Leu Met
     50                  55                  60

TCC AGA CTG AGC ATC AGC AAA GAC AAC TCC AAG AGC CAA GTT TTC TTA       240
Ser Arg Leu Ser Ile Ser Lys Asp Asn Ser Lys Ser Gln Val Phe Leu
 65                  70                  75                  80

AAA ATG AAC AGT CTG CAA ACT GAT GAC ACA GCC ATG TAC TAC TGT GCC       288
Lys Met Asn Ser Leu Gln Thr Asp Asp Thr Ala Met Tyr Tyr Cys Ala
                 85                  90                  95

AGA GAT CGG GGG GCT TAC TGG GGC CAA GGG ACT CTG GTC ACT GTC TCT       336
Arg Asp Arg Gly Ala Tyr Trp Gly Gln Gly Thr Leu Val Thr Val Ser
            100                 105                 110

GCA GGT GGT GGT GGT AGC GGT GGT GGC GGC AGT GGC GGC GGC TCT           384
Ala Gly Gly Gly Gly Ser Gly Gly Gly Gly Ser Gly Gly Gly Gly Ser
        115                 120                 125

CAA ATT GTT CTC ACC CAG TCT CCA GCA ATC ATG TCT GCA TCT CCA GGC       432
Gln Ile Val Leu Thr Gln Ser Pro Ala Ile Met Ser Ala Ser Pro Gly
    130                 135                 140

CAG AAG GTC ACC ATG ACC TGC AGT GCC AGC TCA AGT GTA AGT TAC ATG       480
Gln Lys Val Thr Met Thr Cys Ser Ala Ser Ser Ser Val Ser Tyr Met
145                 150                 155                 160

CAC TGG TAC CAG CAG AAG TCA GGC ACC TCC CCC AAA AGA TGG ATT TAT       528
His Trp Tyr Gln Gln Lys Ser Gly Thr Ser Pro Lys Arg Trp Ile Tyr
                165                 170                 175

GAC ACA TCC AAA CTG GCT TCT GGA GTC CCT GCT CGC TTC AGT GGC AGT       576
Asp Thr Ser Lys Leu Ala Ser Gly Val Pro Ala Arg Phe Ser Gly Ser
            180                 185                 190

GGG TCT GCG ACC TCT TAC TCT CTC ACA ATC AGC AGC ATG GAG GCT GAA       624
Gly Ser Ala Thr Ser Tyr Ser Leu Thr Ile Ser Ser Met Glu Ala Glu
        195                 200                 205
```

```
GAT  GCT  GCC  ACT  TAT  TAC  TGC  CAG  CAG  TGG  AGT  AGT  AAC  CCA  CTC  ACG        672
Asp  Ala  Ala  Thr  Tyr  Tyr  Cys  Gln  Gln  Trp  Ser  Ser  Asn  Pro  Leu  Thr
210                           215                           220

TTC  GGT  GCT  GGG  ACC  AAG  CTG  GAG  CTG  AAA  CGT  AAG                             708
Phe  Gly  Ala  Gly  Thr  Lys  Leu  Glu  Leu  Lys  Arg
225                           230                           235
```

( 2 ) INFORMATION FOR SEQ ID NO:61:

( i ) SEQUENCE CHARACTERISTICS:
        ( A ) LENGTH: 235 amino acids
        ( B ) TYPE: amino acid
        ( D ) TOPOLOGY: linear ( i i ) MOLECULE TYPE: protein ( x i ) SEQUENCE DESCRIPTION: SEQ ID NO:61:

```
Gln  Val  Gln  Leu  Lys  Glu  Ser  Gly  Pro  Gly  Leu  Val  Ala  Pro  Ser  Gln
 1                    5                   10                          15

Ser  Leu  Ser  Ile  Thr  Cys  Thr  Val  Ser  Gly  Phe  Ser  Leu  Thr  Ser  Tyr
                20                   25                     30

Gly  Val  His  Trp  Val  Arg  Gln  Pro  Pro  Gly  Lys  Gly  Leu  Glu  Trp  Leu
           35                    40                         45

Gly  Val  Ile  Trp  Ala  Gly  Gly  Ser  Thr  Asn  Tyr  Asn  Ser  Ala  Leu  Met
      50                     55                     60

Ser  Arg  Leu  Ser  Ile  Ser  Lys  Asp  Asn  Ser  Lys  Ser  Gln  Val  Phe  Leu
65                    70                     75                          80

Lys  Met  Asn  Ser  Leu  Gln  Thr  Asp  Asp  Thr  Ala  Met  Tyr  Tyr  Cys  Ala
                85                     90                          95

Arg  Asp  Arg  Gly  Ala  Tyr  Trp  Gly  Gln  Gly  Thr  Leu  Val  Thr  Val  Ser
           100                   105                        110

Ala  Gly  Gly  Gly  Gly  Ser  Gly  Gly  Gly  Gly  Ser  Gly  Gly  Gly  Gly  Ser
           115                   120                        125

Gln  Ile  Val  Leu  Thr  Gln  Ser  Pro  Ala  Ile  Met  Ser  Ala  Ser  Pro  Gly
     130                   135                   140

Gln  Lys  Val  Thr  Met  Thr  Cys  Ser  Ala  Ser  Ser  Val  Ser  Tyr  Met
145                   150                   155                        160

His  Trp  Tyr  Gln  Gln  Lys  Ser  Gly  Thr  Ser  Pro  Lys  Arg  Trp  Ile  Tyr
                165                   170                       175

Asp  Thr  Ser  Lys  Leu  Ala  Ser  Gly  Val  Pro  Ala  Arg  Phe  Ser  Gly  Ser
                180                   185                       190

Gly  Ser  Ala  Thr  Ser  Tyr  Ser  Leu  Thr  Ile  Ser  Ser  Met  Glu  Ala  Glu
           195                   200                       205

Asp  Ala  Ala  Thr  Tyr  Tyr  Cys  Gln  Gln  Trp  Ser  Ser  Asn  Pro  Leu  Thr
     210                   215                   220

Phe  Gly  Ala  Gly  Thr  Lys  Leu  Glu  Leu  Lys  Arg
225                   230                   235
```

( 2 ) INFORMATION FOR SEQ ID NO:62:

( i ) SEQUENCE CHARACTERISTICS:
        ( A ) LENGTH: 672 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO (ix) FEATURE:
    (A) NAME/KEY: CDS
    (B) LOCATION: 1..669

(xi) SEQUENCE DESCRIPTION: SEQ ID NO:62:

| GAT | GTG | CAG | CTG | GTG | GAG | TCT | GGG | GGA | GGC | TTA | GTG | CAG | CCT | GGA | GGG | 48 |
|---|---|---|---|---|---|---|---|---|---|---|---|---|---|---|---|---|
| Asp | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |
| TCC | CGG | AAA | CTC | TCC | TGT | GCA | GCC | TCT | GGA | TTC | ACT | TTC | AGT | AGC | TTT | 96 |
| Ser | Arg | Lys | Leu | Ser | Cys | Ala | Ala | Ser | Gly | Phe | Thr | Phe | Ser | Ser | Phe | |
| | | | 20 | | | | | 25 | | | | | 30 | | | |
| GGA | ATG | CAC | TGG | GTT | CGT | CAG | GCT | CCA | GAG | AAG | GGG | CTG | GAG | TGG | GTC | 144 |
| Gly | Met | His | Trp | Val | Arg | Gln | Ala | Pro | Glu | Lys | Gly | Leu | Glu | Trp | Val | |
| | | 35 | | | | | 40 | | | | | 45 | | | | |
| GCA | TAT | ATT | AGT | AGT | GGC | AGT | AGT | ACC | ATC | TAC | TAT | GCA | GAC | ACA | GTG | 192 |
| Ala | Tyr | Ile | Ser | Ser | Gly | Ser | Ser | Thr | Ile | Tyr | Tyr | Ala | Asp | Thr | Val | |
| | 50 | | | | | 55 | | | | | 60 | | | | | |
| AAG | GGC | CGA | TTC | ACC | ATC | TCC | AGA | GAC | AAT | CCC | AAG | AAC | ACC | CTG | TTC | 240 |
| Lys | Gly | Arg | Phe | Thr | Ile | Ser | Arg | Asp | Asn | Pro | Lys | Asn | Thr | Leu | Phe | |
| 65 | | | | | 70 | | | | | 75 | | | | | 80 | |
| CTG | CAA | ATG | ACC | AGT | CTA | AGG | TCT | GAG | GAC | ACG | GCC | ATG | TAT | TAC | TGT | 288 |
| Leu | Gln | Met | Thr | Ser | Leu | Arg | Ser | Glu | Asp | Thr | Ala | Met | Tyr | Tyr | Cys | |
| | | | | 85 | | | | | 90 | | | | | 95 | | |
| GCA | AGA | GAT | TAC | GGG | GCT | TAT | TGG | GGC | CAA | GGG | ACT | CTG | GTC | ACT | GTC | 336 |
| Ala | Arg | Asp | Tyr | Gly | Ala | Tyr | Trp | Gly | Gln | Gly | Thr | Leu | Val | Thr | Val | |
| | | | 100 | | | | | 105 | | | | | 110 | | | |
| TCT | GCA | GCT | AGC | CAA | ATT | GTT | CTC | ACC | CAG | TCT | CCA | GCA | ATC | ATG | TCT | 384 |
| Ser | Ala | Ala | Ser | Gln | Ile | Val | Leu | Thr | Gln | Ser | Pro | Ala | Ile | Met | Ser | |
| | | 115 | | | | | 120 | | | | | 125 | | | | |
| GCA | TCT | CCA | GGG | GAG | AAG | GTC | ACC | ATG | ACC | TGC | AGT | GCC | AGT | TCA | AGT | 432 |
| Ala | Ser | Pro | Gly | Glu | Lys | Val | Thr | Met | Thr | Cys | Ser | Ala | Ser | Ser | Ser | |
| | 130 | | | | | 135 | | | | | 140 | | | | | |
| GTA | AGG | TAC | ATG | AAC | TGG | TTC | CAA | CAG | AAG | TCA | GGC | ACC | TCC | CCC | AAA | 480 |
| Val | Arg | Tyr | Met | Asn | Trp | Phe | Gln | Gln | Lys | Ser | Gly | Thr | Ser | Pro | Lys | |
| 145 | | | | | 150 | | | | | 155 | | | | | 160 | |
| AGA | TGG | ATT | TAT | GAC | ACA | TCC | AAA | CTG | TCT | TCT | GGA | GTC | CCT | GCT | CGC | 528 |
| Arg | Trp | Ile | Tyr | Asp | Thr | Ser | Lys | Leu | Ser | Ser | Gly | Val | Pro | Ala | Arg | |
| | | | | 165 | | | | | 170 | | | | | 175 | | |
| TTC | AGT | GGC | AGT | GGG | TCT | GGG | ACC | TCT | TAC | TCT | CTC | ACA | ATC | AGC | AGC | 576 |
| Phe | Ser | Gly | Ser | Gly | Ser | Gly | Thr | Ser | Tyr | Ser | Leu | Thr | Ile | Ser | Ser | |
| | | | 180 | | | | | 185 | | | | | 190 | | | |
| ATG | GAG | GCT | GAA | GAT | GCT | GCC | ACT | TAT | TAC | TGC | CAG | CAG | TGG | AGT | AGT | 624 |
| Met | Glu | Ala | Glu | Asp | Ala | Ala | Thr | Tyr | Tyr | Cys | Gln | Gln | Trp | Ser | Ser | |
| | | 195 | | | | | 200 | | | | | 205 | | | | |
| AAT | CCA | CTC | ACG | TTC | GGT | GCT | GGG | ACC | AAG | CTG | GAG | CTG | AAA | CGT | | 669 |
| Asn | Pro | Leu | Thr | Phe | Gly | Ala | Gly | Thr | Lys | Leu | Glu | Leu | Lys | Arg | | |
| | 210 | | | | | 215 | | | | | 220 | | | | | |
| AAG | | | | | | | | | | | | | | | | 672 |

(2) INFORMATION FOR SEQ ID NO:63:

(i) SEQUENCE CHARACTERISTICS:
        (A) LENGTH: 223 amino acids
        (B) TYPE: amino acid
        (D) TOPOLOGY: linear (ii) MOLECULE TYPE: protein (xi) SEQUENCE DESCRIPTION: SEQ ID NO:63:

| Asp | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Arg | Lys | Leu<br>20 | Ser | Cys | Ala | Ala | Ser<br>25 | Gly | Phe | Thr | Phe | Ser<br>30 | Ser | Phe |
| --- | --- | --- | --- | --- | --- | --- | --- | --- | --- | --- | --- | --- | --- | --- | --- |
| Gly | Met | His<br>35 | Trp | Val | Arg | Gln | Ala<br>40 | Pro | Glu | Lys | Gly | Leu<br>45 | Glu | Trp | Val |
| Ala | Tyr<br>50 | Ile | Ser | Ser | Gly | Ser<br>55 | Ser | Thr | Ile | Tyr | Tyr<br>60 | Ala | Asp | Thr | Val |
| Lys<br>65 | Gly | Arg | Phe | Thr | Ile<br>70 | Ser | Arg | Asp | Asn | Pro<br>75 | Lys | Asn | Thr | Leu | Phe<br>80 |
| Leu | Gln | Met | Thr | Ser<br>85 | Leu | Arg | Ser | Glu | Asp<br>90 | Thr | Ala | Met | Tyr | Tyr<br>95 | Cys |
| Ala | Arg | Asp | Tyr<br>100 | Gly | Ala | Tyr | Trp | Gly<br>105 | Gln | Gly | Thr | Leu | Val<br>110 | Thr | Val |
| Ser | Ala | Ala<br>115 | Ser | Gln | Ile | Val | Leu<br>120 | Thr | Gln | Ser | Pro | Ala<br>125 | Ile | Met | Ser |
| Ala | Ser<br>130 | Pro | Gly | Glu | Lys | Val<br>135 | Thr | Met | Thr | Cys | Ser<br>140 | Ala | Ser | Ser | Ser |
| Val<br>145 | Arg | Tyr | Met | Asn | Trp<br>150 | Phe | Gln | Gln | Lys | Ser<br>155 | Gly | Thr | Ser | Pro | Lys<br>160 |
| Arg | Trp | Ile | Tyr | Asp<br>165 | Thr | Ser | Lys | Leu | Ser<br>170 | Ser | Gly | Val | Pro | Ala<br>175 | Arg |
| Phe | Ser | Gly | Ser<br>180 | Gly | Ser | Gly | Thr | Ser<br>185 | Tyr | Ser | Leu | Thr | Ile<br>190 | Ser | Ser |
| Met | Glu | Ala<br>195 | Glu | Asp | Ala | Ala | Thr<br>200 | Tyr | Tyr | Cys | Gln | Gln<br>205 | Trp | Ser | Ser |
| Asn | Pro<br>210 | Leu | Thr | Phe | Gly | Ala<br>215 | Gly | Thr | Lys | Leu | Glu<br>220 | Leu | Lys | Arg | |

( 2 ) INFORMATION FOR SEQ ID NO:64:

( i ) SEQUENCE CHARACTERISTICS:
        ( A ) LENGTH: 711 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: 1..708

( x i ) SEQUENCE DESCRIPTION: SEQ ID NO:64:

| GAT<br>Asp<br>1 | GTG<br>Val | CAG<br>Gln | CTG<br>Leu | GTG<br>Val<br>5 | GAG<br>Glu | TCT<br>Ser | GGG<br>Gly | GGA<br>Gly | GGC<br>Gly<br>10 | TTA<br>Leu | GTG<br>Val | CAG<br>Gln | CCT<br>Pro | GGA<br>Gly<br>15 | GGG<br>Gly | 48 |
| --- | --- | --- | --- | --- | --- | --- | --- | --- | --- | --- | --- | --- | --- | --- | --- | --- |
| TCC<br>Ser | CGG<br>Arg | AAA<br>Lys | CTC<br>Leu<br>20 | TCC<br>Ser | TGT<br>Cys | GCA<br>Ala | GCC<br>Ala | TCT<br>Ser<br>25 | GGA<br>Gly | TTC<br>Phe | ACT<br>Thr | TTC<br>Phe | AGT<br>Ser<br>30 | AGC<br>Ser | TTT<br>Phe | 96 |
| GGA<br>Gly | ATG<br>Met | CAC<br>His<br>35 | TGG<br>Trp | GTT<br>Val | CGT<br>Arg | CAG<br>Gln | GCT<br>Ala<br>40 | CCA<br>Pro | GAG<br>Glu | AAG<br>Lys | GGG<br>Gly | CTG<br>Leu<br>45 | GAG<br>Glu | TGG<br>Trp | GTC<br>Val | 144 |
| GCA<br>Ala | TAT<br>Tyr | ATT<br>Ile<br>50 | AGT<br>Ser | AGT<br>Ser | GGC<br>Gly | AGT<br>Ser | AGT<br>Ser<br>55 | ACC<br>Thr | ATC<br>Ile | TAC<br>Tyr | TAT<br>Tyr | GCA<br>Ala<br>60 | GAC<br>Asp | ACA<br>Thr | GTG<br>Val | 192 |
| AAG<br>Lys<br>65 | GGC<br>Gly | CGA<br>Arg | TTC<br>Phe | ACC<br>Thr | ATC<br>Ile<br>70 | TCC<br>Ser | AGA<br>Arg | GAC<br>Asp | AAT<br>Asn | CCC<br>Pro<br>75 | AAG<br>Lys | AAC<br>Asn | ACC<br>Thr | CTG<br>Leu | TTC<br>Phe<br>80 | 240 |

| | | | | | | | | | | | | | | | | |
|---|---|---|---|---|---|---|---|---|---|---|---|---|---|---|---|---|
| CTG | CAA | ATG | ACC | AGT | CTA | AGG | TCT | GAG | GAC | ACG | GCC | ATG | TAT | TAC | TGT | 288 |
| Leu | Gln | Met | Thr | Ser | Leu | Arg | Ser | Glu | Asp | Thr | Ala | Met | Tyr | Tyr | Cys | |
| | | | | 85 | | | | 90 | | | | | | 95 | | |
| GCA | AGA | GAT | TAC | GGG | GCT | TAT | TGG | GGC | CAA | GGG | ACT | CTG | GTC | ACT | GTC | 336 |
| Ala | Arg | Asp | Tyr | Gly | Ala | Tyr | Trp | Gly | Gln | Gly | Thr | Leu | Val | Thr | Val | |
| | | | 100 | | | | | 105 | | | | 110 | | | | |
| TCT | GCA | GGT | GGT | GGT | GGT | AGC | GGT | GGT | GGC | GGC | AGT | GGC | GGC | GGC | GGC | 384 |
| Ser | Ala | Gly | Gly | Gly | Gly | Ser | Gly | Gly | Gly | Gly | Ser | Gly | Gly | Gly | Gly | |
| | | | | 115 | | | | | 120 | | | | 125 | | | |
| TCT | CAA | ATT | GTT | CTC | ACC | CAG | TCT | CCA | GCA | ATC | ATG | TCT | GCA | TCT | CCA | 432 |
| Ser | Gln | Ile | Val | Leu | Thr | Gln | Ser | Pro | Ala | Ile | Met | Ser | Ala | Ser | Pro | |
| | | | 130 | | | | 135 | | | | | 140 | | | | |
| GGG | GAG | AAG | GTC | ACC | ATG | ACC | TGC | AGT | GCC | AGT | TCA | AGT | GTA | AGG | TAC | 480 |
| Gly | Glu | Lys | Val | Thr | Met | Thr | Cys | Ser | Ala | Ser | Ser | Ser | Val | Arg | Tyr | |
| 145 | | | | | 150 | | | | | 155 | | | | | 160 | |
| ATG | AAC | TGG | TTC | CAA | CAG | AAG | TCA | GGC | ACC | TCC | CCC | AAA | AGA | TGG | ATT | 528 |
| Met | Asn | Trp | Phe | Gln | Gln | Lys | Ser | Gly | Thr | Ser | Pro | Lys | Arg | Trp | Ile | |
| | | | | 165 | | | | | 170 | | | | | 175 | | |
| TAT | GAC | ACA | TCC | AAA | CTG | TCT | TCT | GGA | GTC | CCT | GCT | CGC | TTC | AGT | GGC | 576 |
| Tyr | Asp | Thr | Ser | Lys | Leu | Ser | Ser | Gly | Val | Pro | Ala | Arg | Phe | Ser | Gly | |
| | | | 180 | | | | | 185 | | | | | 190 | | | |
| AGT | GGG | TCT | GGG | ACC | TCT | TAC | TCT | CTC | ACA | ATC | AGC | AGC | ATG | GAG | GCT | 624 |
| Ser | Gly | Ser | Gly | Thr | Ser | Tyr | Ser | Leu | Thr | Ile | Ser | Ser | Met | Glu | Ala | |
| | | | 195 | | | | | 200 | | | | 205 | | | | |
| GAA | GAT | GCT | GCC | ACT | TAT | TAC | TGC | CAG | CAG | TGG | AGT | AGT | AAT | CCA | CTC | 672 |
| Glu | Asp | Ala | Ala | Thr | Tyr | Tyr | Cys | Gln | Gln | Trp | Ser | Ser | Asn | Pro | Leu | |
| | | 210 | | | | | 215 | | | | 220 | | | | | |
| ACG | TTC | GGT | GCT | GGG | ACC | AAG | CTG | GAG | CTG | AAA | CGT | AAG | | | | 711 |
| Thr | Phe | Gly | Ala | Gly | Thr | Lys | Leu | Glu | Leu | Lys | Arg | | | | | |
| 225 | | | | | 230 | | | | | 235 | | | | | | |

( 2 ) INFORMATION FOR SEQ ID NO:65:

( i ) SEQUENCE CHARACTERISTICS:
        ( A ) LENGTH: 236 amino acids
        ( B ) TYPE: amino acid
        ( D ) TOPOLOGY: linear ( i i ) MOLECULE TYPE: protein ( x i ) SEQUENCE DESCRIPTION: SEQ ID NO:65:

| | | | | | | | | | | | | | | | |
|---|---|---|---|---|---|---|---|---|---|---|---|---|---|---|---|
| Asp | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Arg | Lys | Leu | Ser | Cys | Ala | Ala | Ser | Gly | Phe | Thr | Phe | Ser | Ser | Phe |
| | | | 20 | | | | | 25 | | | | | 30 | | |
| Gly | Met | His | Trp | Val | Arg | Gln | Ala | Pro | Glu | Lys | Gly | Leu | Glu | Trp | Val |
| | | 35 | | | | | 40 | | | | | 45 | | | |
| Ala | Tyr | Ile | Ser | Ser | Gly | Ser | Ser | Thr | Ile | Tyr | Tyr | Ala | Asp | Thr | Val |
| | 50 | | | | | 55 | | | | | 60 | | | | |
| Lys | Gly | Arg | Phe | Thr | Ile | Ser | Arg | Asp | Asn | Pro | Lys | Asn | Thr | Leu | Phe |
| 65 | | | | | 70 | | | | | 75 | | | | | 80 |
| Leu | Gln | Met | Thr | Ser | Leu | Arg | Ser | Glu | Asp | Thr | Ala | Met | Tyr | Tyr | Cys |
| | | | | 85 | | | | | 90 | | | | | 95 | |
| Ala | Arg | Asp | Tyr | Gly | Ala | Tyr | Trp | Gly | Gln | Gly | Thr | Leu | Val | Thr | Val |
| | | | 100 | | | | | 105 | | | | | 110 | | |
| Ser | Ala | Gly | Gly | Gly | Gly | Ser | Gly | Gly | Gly | Gly | Ser | Gly | Gly | Gly | Gly |
| | | | | 115 | | | | | 120 | | | | | 125 | |
| Ser | Gln | Ile | Val | Leu | Thr | Gln | Ser | Pro | Ala | Ile | Met | Ser | Ala | Ser | Pro |
| | | | 130 | | | | | 135 | | | | | 140 | | |
| Gly | Glu | Lys | Val | Thr | Met | Thr | Cys | Ser | Ala | Ser | Ser | Ser | Val | Arg | Tyr |

| 145 | | | | | 150 | | | | | 155 | | | | | 160 |
|---|---|---|---|---|---|---|---|---|---|---|---|---|---|---|---|
| Met | Asn | Trp | Phe | Gln | Gln | Lys | Ser | Gly | Thr | Ser | Pro | Lys | Arg | Trp | Ile |
| | | | | 165 | | | | | 170 | | | | | 175 | |

Tyr Asp Thr Ser Lys Leu Ser Ser Gly Val Pro Ala Arg Phe Ser Gly
            180                     185                     190

Ser Gly Ser Gly Thr Ser Tyr Ser Leu Thr Ile Ser Ser Met Glu Ala
        195                 200                 205

Glu Asp Ala Ala Thr Tyr Tyr Cys Gln Gln Trp Ser Ser Asn Pro Leu
    210                 215                 220

Thr Phe Gly Ala Gly Thr Lys Leu Glu Leu Lys Arg
225                 230                 235

( 2 ) INFORMATION FOR SEQ ID NO:66:

( i ) SEQUENCE CHARACTERISTICS:
        ( A ) LENGTH: 669 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: CDS
        ( B ) LOCATION: 1..666

( x i ) SEQUENCE DESCRIPTION: SEQ ID NO:66:

```
CAG GTG CAG CTG AAG GAG TCA GGA CCT GGC CTG GTG GCG CCC TCA CAG      48
Gln Val Gln Leu Lys Glu Ser Gly Pro Gly Leu Val Ala Pro Ser Gln
 1               5                  10                  15

AGC CTG TCC ATC ACT TGC ACT GTC TCT GGG TTT TCA TTA ACC AGC TAT      96
Ser Leu Ser Ile Thr Cys Thr Val Ser Gly Phe Ser Leu Thr Ser Tyr
            20                  25                  30

GGT GTA CAC TGG GTT CGC CAG CCT CCA GGA AAG GGT CTG GAG TGG CTG     144
Gly Val His Trp Val Arg Gln Pro Pro Gly Lys Gly Leu Glu Trp Leu
        35                  40                  45

GGA GTA ATA TGG GCT GGT GGA AGC ACA AAT TAT AAT TCG GCT CTC ATG     192
Gly Val Ile Trp Ala Gly Gly Ser Thr Asn Tyr Asn Ser Ala Leu Met
    50                  55                  60

TCC AGA CTG AGC ATC AGC AAA GAC AAC TCC AAG AGC CAA GTT TTC TTA     240
Ser Arg Leu Ser Ile Ser Lys Asp Asn Ser Lys Ser Gln Val Phe Leu
65                  70                  75                  80

AAA ATG AAC AGT CTG CAA ACT GAT GAC ACA GCC ATG TAC TAC TGT GCC     288
Lys Met Asn Ser Leu Gln Thr Asp Asp Thr Ala Met Tyr Tyr Cys Ala
                85                  90                  95

AGA GAT CGG GGG GCT TAC TGG GGC CAA GGG ACT CTG GTC ACT GTC TCT     336
Arg Asp Arg Gly Ala Tyr Trp Gly Gln Gly Thr Leu Val Thr Val Ser
            100                 105                 110

GCA GCT AGC CAA ATT GTT CTC ACC CAG TCT CCA GCA ATC ATG TCT GCA     384
Ala Ala Ser Gln Ile Val Leu Thr Gln Ser Pro Ala Ile Met Ser Ala
        115                 120                 125

TCT CCA GGC CAG AAG GTC ACC ATG ACC TGC AGT GCC AGC TCA AGT GTA     432
Ser Pro Gly Gln Lys Val Thr Met Thr Cys Ser Ala Ser Ser Ser Val
    130                 135                 140

AGT TAC ATG CAC TGG TAC CAG CAG AAG TCA GGC ACC TCC CCC AAA AGA     480
Ser Tyr Met His Trp Tyr Gln Gln Lys Ser Gly Thr Ser Pro Lys Arg
145                 150                 155                 160

TGG ATT TAT GAC ACA TCC AAA CTG GCT TCT GGA GTC CCT GCT CGC TTC     528
Trp Ile Tyr Asp Thr Ser Lys Leu Ala Ser Gly Val Pro Ala Arg Phe
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 165 |     |     |     |     | 170 |     |     |     |     | 175 |     |     |
| AGT | GGC | AGT | GGG | TCT | GCG | ACC | TCT | TAC | TCT | CTC | ACA | ATC | AGC | AGC | ATG | 576 |
| Ser | Gly | Ser | Gly | Ser | Ala | Thr | Ser | Tyr | Ser | Leu | Thr | Ile | Ser | Ser | Met |     |
|     |     |     | 180 |     |     |     |     | 185 |     |     |     |     | 190 |     |     |     |
| GAG | GCT | GAA | GAT | GCT | GCC | ACT | TAT | TAC | TGC | CAG | CAG | TGG | AGT | AGT | AAC | 624 |
| Glu | Ala | Glu | Asp | Ala | Ala | Thr | Tyr | Tyr | Cys | Gln | Gln | Trp | Ser | Ser | Asn |     |
|     |     | 195 |     |     |     |     | 200 |     |     |     |     | 205 |     |     |     |     |
| CCA | CTC | ACG | TTC | GGT | GCT | GGG | ACC | AAG | CTG | GAG | CTG | AAA | CGT |     |     | 666 |
| Pro | Leu | Thr | Phe | Gly | Ala | Gly | Thr | Lys | Leu | Glu | Leu | Lys | Arg |     |     |     |
|     | 210 |     |     |     |     | 215 |     |     |     |     | 220 |     |     |     |     |     |
| AAG |     |     |     |     |     |     |     |     |     |     |     |     |     |     |     | 669 |

( 2 ) INFORMATION FOR SEQ ID NO:67:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( x i ) SEQUENCE DESCRIPTION: SEQ ID NO:67:

| Gln | Val | Gln | Leu | Lys | Glu | Ser | Gly | Pro | Gly | Leu | Val | Ala | Pro | Ser | Gln |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | Leu | Ser | Ile | Thr | Cys | Thr | Val | Ser | Gly | Phe | Ser | Leu | Thr | Ser | Tyr |
|     |     |     | 20  |     |     |     |     | 25  |     |     |     |     | 30  |     |     |
| Gly | Val | His | Trp | Val | Arg | Gln | Pro | Pro | Gly | Lys | Gly | Leu | Glu | Trp | Leu |
|     |     | 35  |     |     |     |     | 40  |     |     |     |     | 45  |     |     |     |
| Gly | Val | Ile | Trp | Ala | Gly | Gly | Ser | Thr | Asn | Tyr | Asn | Ser | Ala | Leu | Met |
|     | 50  |     |     |     |     | 55  |     |     |     |     | 60  |     |     |     |     |
| Ser | Arg | Leu | Ser | Ile | Ser | Lys | Asp | Asn | Ser | Lys | Ser | Gln | Val | Phe | Leu |
| 65  |     |     |     |     | 70  |     |     |     |     | 75  |     |     |     |     | 80  |
| Lys | Met | Asn | Ser | Leu | Gln | Thr | Asp | Asp | Thr | Ala | Met | Tyr | Tyr | Cys | Ala |
|     |     |     |     | 85  |     |     |     |     | 90  |     |     |     |     | 95  |     |
| Arg | Asp | Arg | Gly | Ala | Tyr | Trp | Gly | Gln | Gly | Thr | Leu | Val | Thr | Val | Ser |
|     |     |     | 100 |     |     |     |     | 105 |     |     |     |     | 110 |     |     |
| Ala | Ala | Ser | Gln | Ile | Val | Leu | Thr | Gln | Ser | Pro | Ala | Ile | Met | Ser | Ala |
|     |     | 115 |     |     |     |     | 120 |     |     |     |     | 125 |     |     |     |
| Ser | Pro | Gly | Gln | Lys | Val | Thr | Met | Thr | Cys | Ser | Ala | Ser | Ser | Ser | Val |
|     | 130 |     |     |     |     | 135 |     |     |     |     | 140 |     |     |     |     |
| Ser | Tyr | Met | His | Trp | Tyr | Gln | Gln | Lys | Ser | Gly | Thr | Ser | Pro | Lys | Arg |
| 145 |     |     |     |     | 150 |     |     |     |     | 155 |     |     |     |     | 160 |
| Trp | Ile | Tyr | Asp | Thr | Ser | Lys | Leu | Ala | Ser | Gly | Val | Pro | Ala | Arg | Phe |
|     |     |     |     | 165 |     |     |     |     | 170 |     |     |     |     | 175 |     |
| Ser | Gly | Ser | Gly | Ser | Ala | Thr | Ser | Tyr | Ser | Leu | Thr | Ile | Ser | Ser | Met |
|     |     |     | 180 |     |     |     |     | 185 |     |     |     |     | 190 |     |     |
| Glu | Ala | Glu | Asp | Ala | Ala | Thr | Tyr | Tyr | Cys | Gln | Gln | Trp | Ser | Ser | Asn |
|     |     | 195 |     |     |     |     | 200 |     |     |     |     | 205 |     |     |     |
| Pro | Leu | Thr | Phe | Gly | Ala | Gly | Thr | Lys | Leu | Glu | Leu | Lys | Arg |     |     |
|     | 210 |     |     |     |     | 215 |     |     |     |     | 220 |     |     |     |     |

( 2 ) INFORMATION FOR SEQ ID NO:68:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

CCAGAGTCCC TTGGCCCCA                                                                                        1 9

( 2 ) INFORMATION FOR SEQ ID NO:69:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:69:

CTGGTACCAG TGCATGTAA                                                                                        1 9

( 2 ) INFORMATION FOR SEQ ID NO:70:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:70:

GATGGACAGG CTCTGTGAGG                                                                                       2 0